United States Patent [19]

Corominas et al.

[11] Patent Number: 4,927,926
[45] Date of Patent: May 22, 1990

[54] DERIVATIVES OF 7-(1-AZETIDINYL)-1,4-DIHYDRO-4-OXO-3-QUINOLINECARBOXYLIC ACIDS, THEIR PREPARATION AND APPLICATION AS MEDICINES

[75] Inventors: Juan P. Corominas; Jordi F. Constansa; Augusto C. Pinol, all of Barcelona, Spain

[73] Assignee: Laboratorios del Dr. Esteve S.A., Spain

[21] Appl. No.: 290,315

[22] Filed: Dec. 27, 1988

[30] Foreign Application Priority Data

Dec. 29, 1987 [FR] France ................. 87 18289
Jul. 20, 1988 [FR] France ................. 88 09816

[51] Int. Cl.$^5$ ............... C07D 265/34; C07D 215/20; C07D 471/00; C07D 519/02
[52] U.S. Cl. ........................ 544/101; 546/62; 546/68; 546/99; 546/156; 548/950
[58] Field of Search .......... 546/156, 68, 62, 99; 514/229.8, 312; 549/99; 544/101; 548/950

[56] References Cited

U.S. PATENT DOCUMENTS 4,540,690  9/1985  Szmuszkovicz .............. 548/950
4,777,175  10/1988  Culbertson et al. ........... 514/312

FOREIGN PATENT DOCUMENTS 0153163  8/1985  European Pat. Off. .......... 544/101

OTHER PUBLICATIONS

JP 58 72,589 [83 72,589], Chem. Abs., vol. 99, 1983 Abs. 122465v.

Primary Examiner—Mukund J. Shah
Assistant Examiner—E. C. Ward
Attorney, Agent, or Firm—Dressler, Goldsmith, Shore, Sutker & Milnamow, Ltd.

[57] ABSTRACT

The present invention relates to new heterocyclic compounds, derivatives of 7-(1-azetidinyl)-1,4-dihydro-4-oxo-3-quinolinecarboxylic acids, characterized in that they correspond to formula (I)

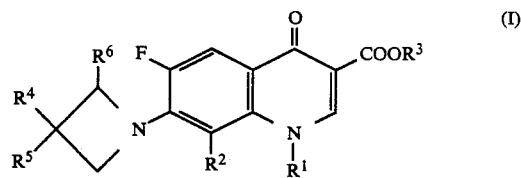

The invention also relates to the preparation of these compounds and their applications as medicines.

8 Claims, No Drawings

DERIVATIVES OF 7-(1-AZETIDINYL)-1,4-DIHYDRO-4-OXO-3-QUINOLINECARBOXYLIC ACIDS, THEIR PREPARATION AND APPLICATION AS MEDICINES

The present invention relates to new derivatives of 1,4-dihydro-4-oxo-3-quinolinecarboxylic acids substituted in the 7 position by a 1-azetidinyl radical which is itself substituted in position 2 and/or position 3.

Azetidines linked to the 7 position of 1,4-dihydro-4-oxo-3-quinolinecarboxylic acids have been very little studied. As far as is known, there are only a small number of publications in the scientific literature which relate to this type of compound. Three Patents (Japan Kokai Tokkyo Koho JP 58/72589 (83/72589), and Eur. Pat. Appl. EP 106489, EP 153163) describe 1-ethyl-7-(3-(ethylamino)methyl-1-azetidinyl)-6,8-difluoro-1,4-dihydro-4-oxo-3-quinolinecarboxylic acid, 9-fluoro-2,3-dihydro-10-(3-hydroxy-1-azetidinyl)-3-methyl-7-oxo-7H-pyrido[1,2,3-de]1,4-benzoxazine-6-carboxylic acid, and 9-fluoro-2,3-dihydro-10-(3-hydroxymethyl-1-azetidinyl)-3-methyl-7-oxo-7-H-pyrido[1,2,3-de]-1,4-benzoxazine-6-carboxylic acid.

The invention relates to heterocyclic compounds represented by formula (I) hereinafter, as well as therapeutically acceptable salts of these compounds:

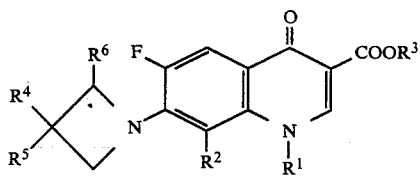

where
$R^1$ represents a lower alkenyl or alkyl radical, a lower haloalkyl radical, a cycloalkyl radical, an amino-alkyl radical, an aryl radical or a substituted aryl radical, particularly one having one or more fluorine atom substituents;
$R^2$ represents a hydrogen atom, a halogen atom, or $R^1$ and $R^2$ may together form an X group;
$R^3$ represents a hydrogen atom or a lower alkyl radical;
$R^4$ and $R^5$ and $R^6$ independently represent a hydrogen atom, a lower alkyl radical, a hydroxyl radical, an amino radical, an aminoalkyl radical, an alkylamino radical, a dialkylamino radical, an alkylaminoalkyl radical, an alkoxy radical, a mesyloxy radical, a hydroxyalkyl radical, a cyano radical, an acylaminoalkyl radical, a carboxyl radical, a carboxamido radical, a carboxyalkyl radical, a halogen atom, an alkylcarboxy radical e.g. acetoxy, an acetamido radical or an acetamidoalkyl radical; in these last two radicals, the terminal free alkyl group may be fluorinated and the nitrogen atom in the acetamidoalkyl radical may carry an alkyl substituent;
X represents —CH₂—CH₂—CHR⁷—, —O—CH₂—CHR⁷— or

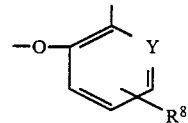

where
$R^7$ represents a hydrogen atom or a lower alkyl radical,
$R^8$ represents a hydrogen atom or a halogen atom, and
Y represents CH or N, with the exception however of compounds of formula (I), in which:
$R^1$ and $R^2$ together form a link represented by a group —O—CH₂—CH(CH₃)— and
$R^3$, $R^4$ and $R^5$ represent a hydrogen atom, and $R^5$ represents a hydroxy radical (OH) or a hydroxymethyl radical (CH₂OH), and of the compound of formula (I) in which:
$R^1$ represents an ethyl radical
$R^2$ represents a fluorine atom
$R^3$, $R^4$ and $R^6$ represent hydrogen atoms, and
$R^5$ represents an ethylaminomethyl radical (CH₃CH₂NHCH₂).

Certain compounds according to the invention are more precisely represented by the general formula (Ia)

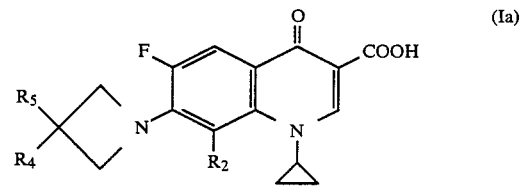

in which $R_2$, $R_4$ and $R_5$ have the same meaning as hereinbefore.

The invention also relates to a pharmaceutical composition containing a compound of formula (I) or one of its pharmaceutically acceptable salts in sufficient quantity to confer efficient antimicrobial activity.

Moreover, the invention relates to processes for preparing compounds of formula (I) and their pharmaceutically acceptable salts.

Throughout this description the term lower alkyl will designate linear or branched hydrocarbon radicals preferably containing 1 to 4 carbon atoms.

The compounds of the invention represented by formula (I) may be prepared by various processes. For instance, one process comprises reacting a heterocyclic compound of formula (II)

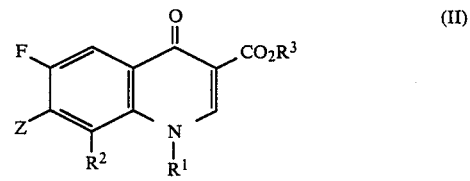

where $R^1$, $R^2$ and $R^3$ have the same meaning as hereinbefore, and Z represents a halogen atom; with a compound represented by formula (III)

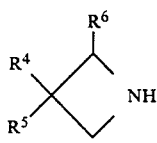

(III)

where $R^4$ and $R^5$ and $R^6$ have the same meaning as hereinbefore.

The reaction may be carried out in a large number of solvents. Examples of such solvents are lower alcohols such as ethanol, isopropanol etc., ethers such as tetrahydrofuran, dioxane, diglyme, etc., nitriles such as acetonitrile, pyridine, dimethyl sulphoxide, dimethylformamide and hexamethylphosphorotriamide.

The above reaction may be carried out in the presence of an acid-acceptor, in a quantity at least approximately between 1 and 2 moles per mole of compound of formula (II). Examples of appropriate acid-acceptors which may be mentioned are alkali metal hydroxides, inorganic carbonates, and tertiary amines such as triethylamine.

The above reaction may be carried out under pressure, i.e. at a pressure of about 1 to 15 kg/cm$^2$, and at a temperature of about 50° to 250° C. for a duration of about 2 to 24 hours.

The heterocyclic compounds of formula (II) that may be used as starting materials for preparing the compounds of the invention represented by formula (I) are known compounds, as described for example by H. Koga, A. Itoh, S. Murayama, S. Suzue and T. Irikura in *J. Med. Chem.*, 1980, 23, 1358.

On the other hand, compounds of formula (III) which are other starting materials for preparing the compounds of the invention represented by formula (I) are known, or are synthesised as described for example in various articles (A. G. Anderson and R. Lok, *J. Org. Chem.*, 1972 37, 3953, R. H. Higgins and N. H. Cromwell, *J. Heterocycl. Chem.*, 1971, 8, 1059).

The compounds of the invention represented by formula (I) may also be prepared by a process which comprises reacting a heterocyclic compound of formula (II), where $R^1$, $R^2$ and $R^3$ have the same meaning as hereinbefore, and Z represents an amino radical, with a compound represented by formula (IV)

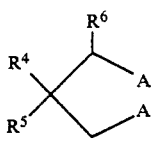

(IV)

where $R^4$ and $R^5$ and $R^6$ have the same meaning as hereinbefore, and A represents a halogen atom, a hydroxyl radical, a lower alkylsulphonyloxy radical or an arylsulphonyloxy radical.

The reaction may be carried out in solvents such as lower alcohols or dipolar non-protonic solvents, such as dimethylsulphoxide, dimethylformamide and hexamethylphosphorotriamide.

The above reaction may be carried out in the presence of an appropriate acid-acceptor, such as alkali metal hydroxides, inorganic carbonates, and tertiary amines such as pyridine or triethylamine.

The above reaction may be carried out at atmospheric pressure or at a pressure of about 1 to 15 kg/cm$^2$, and at a temperature of about 10° to 50° C. for a duration of about 1 to 5 days and afterwards at a temperature of about 50° to 150° C. for a duration of about 8 to 72 hours.

The heterocyclic compounds of formula (II) in which Z represents an amino radical, which may be used as starting materials for preparing the compounds of the invention represented by formula (I) are known compounds, as described for example in Patent EP 0 134 165 and in two publications (T. Uno, M. Takamatsu, Y. Inone, Y. Kawahata, K. Iuchi, G. Tsukamoto, *J. Med. Chem.*, 1987, 30, 2163; and by H. Koga, A. Itoh, S. Murayama, S. Suzue and T. Irikura in *J. Med. Chem.*, 1980, 23, 1358). On the other hand, the compounds of formula (IV), which are other starting materials, are commercial products.

Among the compounds represented by formula (I), those where $R^3$ repesents a hydrogen atom and/or $R^4$ or $R^5$ or $R^6$ represent an amino radical, an aminoalkyl radical, an alkylamino radical, an alkylaminoalkyl radical, may be prepared by hydrolysis of those compounds represented by formula (I) where $R^3$ represents a lower alkyl radical and/or $R^4$ or $R^5$ or $R^6$ represent an acylamino radical, an acylaminoalkyl radical, an alkylacylamino radical or an alkylacylaminoalkyl radical.

The hydrolysis reaction may be carried out by conventional processes for example in the presence of a conventional catalyst, such as a basic compound, for example sodium hydroxide, potassium hydroxide and similar compounds, a mineral acid such as sulphuric acid, hydrochloric acid, or an organic acid such as an aromatic sulphonic acid and similar compounds.

In a general way, the reaction may be carried out in a conventional solvent such as water, alcohols, dioxane, acetone or a mixture of these. Reaction temperature is generally between the prevailing laboratory temperature and 150° C., for a duration of about 2 to 24 hours.

The preparation of new derivatives according to the invention will be shown in the following examples. Some typical uses in the various fields of application will also be described.

The examples hereinafter, given solely by way of illustration, must nevertheless in no way limit the scope of the invention.

EXAMPLE 1

Method A

Preparation of ethyl 1-cyclopropyl-6,8-difluoro-7-(3-hydroxy-1-azetidinyl)-1,4-dihydro-4-oxo-3-quinolinecarboxylate.

A solution of 1.22 g (3.92 mmoles) of ethyl 1-cyclopropyl-6,7,8-trifluoro-1,4-dihydro-4-oxo-3-quinolinecarboxylate, 0.86 g (7.85 mmoles) of 3hydroxyazetidine hydrochloride, 2 g (19.8 mmoles) of triethylamine and 20 ml of dimethyl sulphoxide (DMSO) is heated for 4 hours at 80° C. The solution is allowed to cool and is added to a mixture of ice and water, giving a precipitate which is filtered and washed with water. The solid is dried under vacuum yielding 1.40 g (97%) of ethyl 1-cyclopropyl-6,8-difluoro-7-(3-hydroxy-1-azetidinyl)-1,4-dihydro-4-oxo-3-quinolinecarboxylate melting at 260°-270° C.

Spectroscopic data:

$^1$H NMR, δ, [DMSO-d$_6$]: 1.08 (d, 4H, J=5 Hz); 1.26 (t, 3H, J=7 Hz); 3.60–4 80 (m, 6H); 5.66 (d, 1H, J=4 Hz); 7.52 (d, 1H, J=13.5 Hz); 8.32 (s, 1H).

IR (KBr): 3300; 1725; 1615 cm$^{-1}$.

Method B

Preparation of ethyl 1-cyclopropyl-6,8-difluoro-7-(3-hydroxy-1-azetidinyl)-1,4-dihydro-4-oxo-3-quinolinecarboxylate A solution of 0.8 g (2.60 mmoles) of ethyl 7-amino-1-cyclopropyl-6,8-difluoro-1,4-dihydro-4-oxo-3-quinolinecarboxylate, 0.33 g (2.60 mmoles) of 1,3-dichloro-2-propanol and 25 ml of pyridine is agitated for 3 days, protected from light at ambient temperature; then left refluxing for 3 days and more. The solution is concentrated almost to dryness, poured onto water giving a precipitate which is filtered and washed with water. The solid is dried under vacuum, yielding 0.52 g (55%) of ethyl 1-cyclopropyl-6,8-difluoro-7-(3-hydroxy-1-azetidinyl)-1,4-dihydro-4-oxo-3-quinolinecarboxylate. Its melting point and spectroscopic data are identical to those of the derivative obtained according to method A.

EXAMPLE 2

Method C

Preparation of 1-cyclopropyl-6,8-difluoro-7-(3-hydroxy-1-azetidinyl)-1,4-dihydro-4-oxo-3-quinolinecarboxylic acid.

A solution of 0.4 g (1.10 mmoles) of ethyl 1-cyclopropyl-6,8-difluoro-7-(3-hydroxy-1-azetidinyl)-1,4-dihydro-4-oxo-3-quinolinecarboxylate, 2 ml of ethanol and 10 ml of 0.5N sodium hydroxide is left to reflux for 1.5 hours. It is then allowed to cool, diluted with water, adjusted to pH 5 and a precipitate is obtained which is filtered and washed with water. The solid is dried under vacuum yielding 0.37 g (100%) of 1-cyclopropyl-6,8-difluoro-7-(3-hydroxy-1-azetidinyl)-1,4-dihydro-4-oxo-3-quinolinecarboxylic acid melting at 286°–288° C.

Spectroscopic data $^1$H NMR, δ, [DMSO-d$_6$, TFA]: 1.13 (m, 4H); 4.10 (m, 3H); 4.55 (m, 3H); 7.75 (d, 1H, J=13 Hz); 8.55 (s, 1H). IR (KBr): 3400; 1700; 1625 cm$^{-1}$.

Method D

Preparation of 1-cyclopropyl-6,8-difluoro-7-(3-hydroxy-1-azetidinyl)-1,4-dihydro-4-oxo-3-quinolinecarboxylic acid A solution of 0.9 g (3.2 mmoles) of 1-cyclopropyl-6,7,8-trifluoro-1,4-dihydro-4-oxo-3-quinolinecarboxylic acid, 0.7 g (6.4 mmoles) of 3-hydroxyazetidine, 1.6 g (16.0 mmoles) of triethylamine and 15 ml of DMSO is heated to 80° C. for 4 hours. It is allowed to cool, added to a mixture of ice and water, and adjusted to pH 5 giving a precipitate which is filtered and washed with water. The solid is dried under vacuum to yield 0.86 g (80%) of 1-cyclopropyl-6,8-difluoro-7-(3-hydroxy-1-azetidinyl)-1,4-dihydro-4-oxo-3-quinolinecarboxylic acid melting at 286°–288° C. Spectroscopic data are identical to those of method C.

EXAMPLE 3

Preparation of ethyl 1-cyclopropyl-6,8-difluoro-7-(3-mesyloxy-1-azetidinyl)-1,4-dihydro-4-oxo-3-quinolinecarboxylate 6.3 g (55.0 mmoles) of mesyl chloride are slowly added to a solution of 1.0 g (2.75 mmoles) of ethyl 1-cyclopropyl-6,8-difluoro-7-(3-hydroxy-1-azetidinyl)-1,4-dihydro-4-oxo-3-quinolinecarboxylate in 50 ml of pyridine cooled to 0° C., and the reaction is maintained at 0° C. for 3 hours. The solution is added to a mixture of ice and water giving a precipitate which is filtered and washed with water. The solid is dried under vacuum yielding 0.9 g (73%) of ethyl 1-cyclopropyl-6,8-difluoro-7-(3-mesyloxy-1-azetidinyl)-1,4-dihydro-4-oxo-3-quinolinecarboxylate melting at 191°–193° C.

Spectroscopic data $^1$H NMR, δ, [CDCl$_3$]: 1.11 (b, 4H); 1.38 (t, 3H, J=7 Hz); 3.08 (s, 3H); 3.80 (m, 1H); 4.36 (q, 2H, J=7 Hz); 4.53 (m, 2H); 4.70 (m, 2H); 5.36 (m, 1H); 7.83 (dd, 1H, J=13 Hz, J'=1 Hz); 8.45 (s, 1H).

IR 'KBr): 1720; 1615; 1475; 1340; 1165 cm$^{-1}$.

EXAMPLE 4

Preparation of ethyl 7-(3-acetamidomethyl-1-azetidinyl)-1-cyclopropyl-6,8-difluoro-1,4-dihydro-4-oxo-3-quinolinecarboxylate.

A solution of 1.0 g (3.2 mmoles) of ethyl 1-cyclopropyl-6,7,8-trifluoro-1,4-dihydro-4-oxo-3-quinolinecarboxylate, 1.05 g (6.4 mmoles) of 3-acetamidomethylazetidine hydrochloride, 1.6 g (16 mmoles) of triethylamine and 20 ml of DMSO is heated to 80° C. for 4 hours. It is allowed to cool, poured onto a mixture of ice and water giving a precipitate which is filtered and washed with water. The solid is dried under vacuum yielding 0.93 g (69%) of ethyl 7-(3-acetamidomethyl-1-azetidinyl)-1-cyclopropyl-6,8-difluoro-1,4-dihydro-4-oxo-3-quinolinecarboxylate melting at 170°–190° C.

Spectroscopic data $^1$H NMR, δ, [CDCl$_3$]: 1.11 (m, 4H); 1.37 (t, 3H, J=7. Hz); 2.04 (s, 3H); 2.97 (m, 1H); 3.4–4.7 (m, 9H); 6.64 (m, 1H); 7.67 (d, 1H, J=13 Hz); 8.44 (s, 1H). IR(KBr): 3300; 1720, 1650; 1615; 1545 cm$^{-1}$.

EXAMPLE 5

Preparation of 1-cyclopropyl-6,8-difluoro-7-(3-carboxy-1-azetidinyl)-1,4-dihydro-4-oxo-3-quinolinecarboxylic acid.

A mixture of 0.3 g (1 mmole) of 1-cyclopropyl-6,7,8-trifluoro-1,4-dihydro-4-oxo-3-quinolinecarboxylic acid, 0.2 g (2 mmoles) of azetidine-3-carboxylic acid, 0.5 g (5 mmoles) of triethylamine and 5 ml of DMSO is heated to 100° C. for 24 hours.

The mixture is allowed to cool, added to a mixture of ice and water, filtered and the product recrystallised from DMF/H$_2$O (15:2) to yield 0.11 g (28%) of 1-cyclopropyl-6,8-difluoro-7-(3-carboxy-1-azetidinyl)-1,4-dihydro-4-oxo-3-quinolinecarboxylic acid, melting at 251°–5° C.

Spectroscopic data $^1$H NMR, δ, [DMSO-d$_6$]: 1.2 (m, 4H); 3.55 (m, 1H); 3.95 (m, 1H); 4.52 (m, 5H); 7.65 (d, 1H, J=12 Hz); 8.55 (s, 1H).

IR(KBr): 2920, 1725, 1630, 1460 cm$^{-1}$.

EXAMPLE 6

Preparation of 1-cyclopropyl-6,8-difluoro-7-(3-carbamoyl-1-azetidinyl)-1,4-dihydro-4-oxo-3-quinolinecarboxylic acid.

A mixture of 0.57 g (2 mmoles) of 1-cyclopropyl-6,7,8-trifluoro-1,4-dihydro-4-oxo-3-quinolinecarboxylic acid, 0.35 g (2.6 mmoles) of azetidine-3-carboxamide hydrochloride and 0.6 g (6 mmoles) of triethylamine in 5 ml of DMSO is heated to 100° C. for 2 hours.

The mixture is allowed to cool, and added to a water-/acetic acid mixture. Filtering and washing with water yield 0.62 g (66%) of 1-cyclopropyl-6,8-difluoro-7-(3-carbamoyl-1-azetidinyl)-1,4-dihydro-4-oxo-3-quinolinecarboxylic acid melting at 295°–8° C.

Spectroscopic data $^1$H NMR, δ, [DMSO-6d, TFA]; 1.15 (m, 4H); 3.55 (m, 1H); 4.05 (m, 1H); 4.45 (m, 4H); 7.1 (s, 1H); 7.55 (m, 2H); 8.6 (s, 1H).

IR(KBr): 3390, 3190, 1740, 1665, 1640, 1450 cm$^{-1}$.

EXAMPLE 7

Preparation of 1-cyclopropyl-6,8-difluoro-7-(3-cyano-1-azetidinyl)-1,4-dihydro-4-oxo-3-quinolinecarboxylic acid A solution of 0.57 g (1.5 mmoles) of 1-cyclopropyl-6,8-difluoro-7-(3-carbamoyl-1-azetidinyl)-1,4-dihydro-4-oxo-3-quinolinecarboxylic acid (example 6) in 12 ml of acetic anhydride is heated under reflux for 24 hours. Cooling, filtering and washing with water and ethanol yield 0.15 g (27%) of 1-cyclopropyl-6,8-difluoro-7-(3-cyano-1-azetidinyl)-1,4-dihydro-4-oxo-3-quinolinecarboxylic acid melting at >325° C.

Spectroscopic data $^1$H NMR, δ, [DMSO-6d, TFA]: 1.20 (m, 4H); 3.95 (m, 1H); 4.6 (m, 5H); 7.75 (d, J=12 Hz, 1H); 8.6 (s, 1H).
IR(KBr): 2250, 1735, 1635, 1650 cm$^{-1}$.

EXAMPLE 8

Preparation of 1-cyclopropyl-6,8-difluoro-7-(3-methyl-3-hydroxy-1-azetidinyl)-1,4-dihydro-4-oxo-3-quinolinecarboxylic acid A mixture of 0.9 g (2.9 mmoles) of ethyl 1-cyclopropyl-6,7,8-trifluoro-1,4-dihydro-4-oxo-3-quinolinecarboxylate, 0.54 g (4.3 mmoles) of 3-hydroxy-3-methylazetidine hydrochloride, 1 g (10.8 mmoles) of triethylamine and 10 ml of pyridine is heated under reflux for 10 hours. The product is cooled, and diluted with water. Filtering and washing yields 0.95 g (89%) of ethyl 1-cyclopropyl-6,8-difluoro-7-(3-methyl-3-hydroxy-1-azetidinyl)-1,4-dihydro-4-oxo-3-quinolinecarboxylate which is then hydrolysed by heating a mixture of 0.38 g (1 mmole) of this ester with 1.5 ml of ethanol, and 8 ml of 0.5N sodium hydroxide under reflux for 3 hours. The mixture is cooled, filtered and acidified with acetic acid.

Filtering and washing with water yield 0.34 g (97%) of 1-cyclopropyl-6,8-difluoro-7-(3-methyl-3-hydroxy-1-azetidinyl)-1,4-dihydro-4-oxo-3-quinolinecarboxylic acid melting at 290°–4° C.

Spectroscopic data:

$^1$H NMR, δ, [DMSO-6d, TFA]: 1.16 (d, J=7 Hz, 4H); 1.48 (s, 3H); 4.05 (m, 1H); 4.26 (m, 4H); 7.66 (dd J=13 Hz, J=2 Hz, 1H); 8.56 (s, 1H).
IR(KBr): 3450, 1725, 1630, 1530, 1460 cm$^{-1}$.

EXAMPLE 9

Preparation of 7-(3-trifluoroacetamidomethyl-1-azetidinyl)-1-cyclopropyl-6,8-difluoro-1,4-dihydro-4-oxo-3-quinolinecarboxylic acid A solution of 0.8 g (2.8 mmoles) of 1-cyclopropyl-6,7,8-trifluoro-1,4-dihydro-4-oxo-3-quinolinecarboxylic acid, 0.92 g (4.2 mmoles) of 3-trifluoroacetamidomethylazetidine hydrochloride, 8 ml of pyridine and 1.7 g of triethylamine is heated under reflux for 3 hours. It is then evaporated under vacuum, diluted with water and filtered. 1.12 g (88.9%) of 7-(3-trifluoroacetamidomethyl-1-azetidinyl)-1-cyclopropyl-6,8-difluoro-1,4-dihydro-4-oxo-3-quinolinecarboxylic acid are obtained, melting at 145°–150° C.

Spectroscopic data:

$^1$H NMR, δ, [DMSO-6d, TFA]: 1.10 (m, 4H); 3.0 (m, 1H); 3.50 (m, 2H); 4.20 (m, 3H); 4.50 (m, 2H); 7.65 (d J=13 Hz 1H); 8.45 (s, 1H).
IR(KBr): 3300, 1725, 1630, 1460 cm$^{-1}$.

EXAMPLE 10

Preparation of 7-(3-aminomethyl-1-azetidinyl)-1-cyclopropyl-6,8-difluoro-1,4-dihydro-4-oxo-3-quinolinecarboxylic acid.

A solution of 0.8 g (1.6 mmoles) of 7-(3-trifluoroacetamidomethyl-1-azetidinyl)-1-cyclopropyl-6,8-difluoro-1,4-dihydro-4-oxo-3-quinolinecarboxylic acid (example 9) in 30 ml of 1N sodium hydroxide is maintained at 80° C. for 3 hours, cooled and acidified with acetic acid. Filtering and washing yield 0.41 g (65%) of 7-(3-aminomethyl-1-azetidinyl)-1-cyclopropyl-6,8-difluoro-1,4-dihydro-4-oxo-3-quinolinecarboxylic acid melting at 190°–195° C.

Spectroscopic data:

$^1$H NMR, δ, [DMSO-6d, TFA]: 1.16 (m, 4H); 3.0 (m, 2H); 4.25 (m, 5H); 7.71 (m, 3H); 8.55 (s, 1H).
IR(KBr): 3500, 1730, 1680, 1630 cm$^{-1}$.

EXAMPLE 11

Preparation of 1-cyclopropyl-6,8-difluoro-7-(3-mesyloxy-1-azetidinyl)-1,4-dihydro-4-oxo-3-quinolinecarboxylic acid A solution of 0.2 g (0.4 mmole) of ethyl 1-cyclopropyl-6,8-difluoro-7-(3-mesyloxy-1-azetidinyl)-1,4-dihydro-4-oxo-3-quinolinecarboxylate (example 3) in 6 ml of 0.5N sodium hydroxide and 1 ml of ethanol is refluxed for 1 hour. It is evaporated under vacuum, and acetic acid is added. Filtering and washing yield 0.18 g (96%) of 1-cyclopropyl-6,8-difluoro-7-(3-mesyloxy-1-azetidinyl)-1,4-dihydro-4-oxo-3-quinolinecarboxylic acid melting at 240°–4° C.

Spectroscopic data $^1$H NMR, δ, [DMSO-6d, TFA]: 1.19 (m, 4H); 3.3 (s, 3H); 4.06 (m, 2H); 4.54 (m, 2H); 4.77 (m, 2H); 5.44 (m, 1H); 7.68 (d, J=14 Hz 1H); 8.57 (s, 1H).

EXAMPLE 12

Preparation of 7-[3-(N'-ethyl-N'-trifluoroacetamidomethyl)-1-azetidinyl]-6,8-difluoro-1,4-dihydro-1-cyclopropyl-4-oxo-3-quinolinecarboxylic acid A solution of 1.0 g (3.5 mmoles) of 1-cyclopropyl-6,7,8-trifluoro-1,4-dihydro-4-oxo-3-quinolinecarboxylic acid, 1.4 g (5.7 mmole) of 3-(N'-ethyl-N'-trifluoroacetamidomethyl)-azetidine hydrochloride, 9 ml of pyridine and 2.9 g (28.5 mmoles) of triethylamine is heated under reflux for 2 hours. It is evaporated under vacuum and diluted with a 1:1 solution of ethanol in water. After filtering and washing, 1.3 g (78%) of 7-[3-(N'-ethyl-N'-trifluoroacetamidomethyl)-1-azetidinyl]-6,8-difluoro-1,4-dihydro-1-cyclopropyl-4-oxo-3-quinolinecarboxylic acid are obtained, melting at 208°–12° C.

Spectroscopic data:

¹H NMR, δ, [DMSO-6d, TFA]: 1.15 (m, 7H); 3.0 (m, 1H); 3.35 (m, 2H); 3.72 (m, 2H); 4.1 (m, 3H); 4.45 (m, 2H); 7.6 (d, J=13 Hz 1H); 8.55 (s, 1H).
IR(KBr): 1729, 1688, 1466, 1326 cm⁻¹.

EXAMPLE 13

Preparation of 7-(3-ethylaminomethyl-1-azetidinyl)-6,8-difluoro-1,4-dihydro-1-cyclopropyl-4-oxo-3-quinolinecarboxylic acid A solution of 0.7 g (1.5. mmoles) of 7-[3-(N'-ethyl-N'-trifluoroacetamidomethyl)-1-azetidinyl]-6,8-difluoro-1,4-dihydro-1-cyclopropyl-4-oxo-3-quinolinecarboxylic acid (example 12) in 9 ml of 1N sodium hydroxide and 3 ml of ethanol is refluxed for 3 hours. It is cooled, and acetic acid is added. After filtering and washing with cold ethanol, 0.37 g (66%) of 7-(3-ethylaminomethyl-1-azetidinyl)-6,8-difluoro-1,4-dihydro-1-cyclopropyl-4-oxo-3-quinolinecarboxylic acid are obtained, melting at 237°–42° C.

Spectroscopic data:

¹H NMR, δ, [DMSO-6d, TFA]: 1.2 (m, 7H); 2.6 (m, 1H); 3.0 (m, 2H); 3.25 (m, 2H); 4.05 (m, 1H); 4.25 (m, 2H); 4.5 (m, 2H); 7.6 (d, J=13 Hz, 1H); 8.5 (s, 1H).
IR(KBr): 3300, 1624, 1474, 1323 cm⁻¹.

EXAMPLE 14

Preparation of 1-cyclopropyl-6,8-difluoro-1,4-dihydro-7-(1-azetidinyl)-4-oxo-3-quinolinecarboxylic acid A mixture of 0.6 g (2.1 mmoles) of 1-cyclopropyl-1,4-dihydro-6,7,8-trifluoro-4-oxo-3-quinolinecarboxylic acid with 0.25 g (4.4 mmoles) of azetidine, 8 ml of pyridine and 1 ml of triethylamine is maintained at 110°–120° C. for 2 hours in a closed vessel. After cooling, evaporating under vacuum, filtering and washing, 0.6 g (88%) of 1-cyclopropyl-6,8-difluoro-1,4-dihydro-7-(1-azetidinyl)-4-oxo-3-quinolinecarboxylic acid are obtained, melting at 289°–93° C.

Spectroscopic data:

¹H NMR, δ, [DMSO-6d]: 1.15 (m, 4H); 2.50 (m, 2H); 4.07 (m, 1H); 4.45 (m, 4H); 7.70 (d, J=13 Hz, 1H); 8.58 (s, 1H).
IR(KBr): 1724, 1629, 1460 cm⁻¹.

EXAMPLE 15

Preparation of 1-cyclopropyl-6,8-difluoro-7-(3-methyl-3-trifluoroacetamido-1-azetidinyl)-4-oxo-3-quinolinecarboxylic acid.

A solution of 1 g (3.5 mmoles) of 1-cyclopropyl-6,7,8-trifluoro-4-oxo-3-quinolinecarboxylic acid, 1.15 g (5.3 mmoles) of 3-methyl-3-trifluoroacetamidoazetidine hydrochloride, 2 ml of triethylamine in 10 ml of pyridine is refluxed for 3 hours.

The solution is evaporated under vacuum, water is added, the product is acidified with acetic acid and filtered. After washing with water and cold ethanol, 1.15 g (73%) of 1-cyclopropyl-6,8-difluoro-1,4-dihydro-7-(3-methyl-3-trifluoroacetamido-1-azetidinyl)-4-oxo-3-quinolinecarboxylic acid are obtained, melting at 208°–213° C.

Spectroscopic data:

¹H NMR, δ, [DMSO-d₆-TFA]: 1.1 (broadened, 4H9; 1.5 (s, 3H); 4.0 (m, 1H); 4.2 (m, 2H); 4.5 (m, 2H); 7.5 (m, 1H); 8.5 (s, 1H); 9.8 (s, 1H).

IR(KBr): 3320, 1725, 1628, 1465 cm⁻¹.

EXAMPLE 16

Method E

Preparation of 1-cyclopropyl-6,8-difluoro-1,4-dihydro-7-(3-methyl-3-amino-1-azetidinyl)-4-oxo-3-quinolinecarboxylic acid A solution of 0.8 g (1.8 mmoles) of 1-cyclopropyl-6,8-difluoro-1,4-dihydro-7-(3-methyl-3-trifluoroacetamido-1-azetidinyl)-4-oxo-3-quinolinecarboxylic acid (example 11) in a mixture of 10 ml of 1N sodium hydroxide and 2 ml of ethanol is refluxed for 3 hours. It is evaporated under vacuum and acetic acid is added. The product is filtered and washed with water and ethanol. 0.35 g (55%) of 1-cyclopropyl-6,8-difluoro-1,4-dihydro-7-(3-methyl-3-amino-1-azetidinyl)-4-oxo-3-quinolinecarboxylic acid are obtained having a melting point of 298°–300° C.

Spectroscopic data:

¹H NMR, δ, [DMSO-d₆, TFA]: 1.18 (d, 4H, J=6.2 Hz); 1.64 (s, 3H), 4.05 (m, 1H); 4.42 (m, 4H); 7.74 (dd 1H, J=12.5 Hz, J'=1.7 Hz); 8.61 (s, 1H).
IR(KBr): 3100, 1627, 1466, 1319 cm⁻¹.

Method F

Preparation of 1-cyclopropyl-6,8-difluoro-1,4-dihydro-7-(3-methyl-3-amino-1-azetidinyl)-4-oxo-3-quinolinecarboxylic acid A mixture of 0.23 g (0.82 mmoles) of 1-cyclopropyl-6,7,8-trifluoro-4-oxo-1,4-dihydro-3-quinolinecarboxylic acid, 0.26 g (1.64 mmoles) of 3-methyl-3-aminoazetidine dihydrochloride and 0.5 ml of triethylamine is refluxed in 10 ml of pyridine for 2 hours. Filtering and washing with water and ethanol yield 0.250 g (87%) of 1-cyclopropyl-6,8-difluoro-1,4-dihydro-7-(3-methyl-3-amino-1-azetidinyl)-4-oxo-3-quinolinecarboxylic acid having a melting point and spectroscopic data identical to those of the derivative obtained by Method E.

EXAMPLE 17

Preparation of 1-cyclopropyl-6,8-difluoro-7-(3-acetoxy-1-azetidinyl)-b 1,4-dihydro-4-oxo-3-quinolinecarboxylic acid 0.7 g (2 mmoles) of 1-cyclopropyl-6,8-difluoro-7-(3-hydroxy-1-azetidinyl)-1,4-dihydro-4-oxo-3-quinolinecarboxylic acid (example 2) are dissolved in 20 ml of pyridine. 0.64 g (6.2 mmoles) of acetic anhydride are added slowly and the solution is left at room temperature for 24 hours. It is diluted with water, filtered, and the precipitate is washed. This yields 0.54 g (68%) of 1-cyclopropyl-6,8-difluoro-7-(3-acetoxy-1-azetidinyl)-1,4-dihydro-4-oxo-3-quinolinecarboxylic acid melting at 259°–262° C.

Spectroscopic data:

¹H NMR, δ, [DMSO-6d-TFA]: 1.2 (d, J=6 Hz, 4H); 2.1 (s, 3H); 4.05 (q, J=6 Hz, 1H); 4.4 (m, 2H); 4.8 (m. 2H); 5.3 (m, 1H), 7.7 (dd, J=13 Hz, J'=2 Hz, 1H); 8.60 (s, 1H).
IR(KBr): 1742, 1727, 1626, 1481 cm⁻¹.

EXAMPLE 18

Preparation of 1-cyclopropyl-6-fluoro-7-(3-hydroxy-1-azetidinyl)-1,4-dihydro-4-oxo-3-quinolinecarboxylic acid A mixture of 1 g (3.5 mmoles) of 1-cyclopropyl-7-chloro-6-fluoro-4-oxo-1,4-dihydro-quinoline-3-carboxylic acid, 0.77 g (7.9 mmoles) of 3-hydroxyazetidine hydrochloride, 2.15 g (21.3 mmoles) of triethylamine is heated to 160° C. in 10 ml of dimethyl sulphoxide for 6 hours. The mixture is cooled, diluted with water and acidified with acetic acid. After filtering and recrystallising from dimethylformamide 0.3 g (27%) of 1-cyclopropyl-6-fluoro-7-(3-hydroxy-1-azetidinyl)-1,4-dihydro-4-oxo-3-quinolinecarboxylic acid are obtained, melting at 296°-8° C.

Spectroscopic data:

$^1$H NMR, $\delta$, [DMSO-6d, TFA]: 1.14 (m, 4H): 3.95 (m, 3H); 4.40 (m, 3H); 6.90 (d, 1H, J=8 Hz); 7.7 (d, 1H, J=12 Hz); 8.53 (s, 1H).
IR(KBr): 3406, 1703, 1632, 1524, 1340 cm$^{-1}$.

EXAMPLE 19

Preparation of 1-(4-fluorophenyl)-6,8-difluoro-7-(3-methyl-3-trifluoroacetamido-1-azetidinyl)-1,4-dihydro-4-oxo-3-quinolinecarboxylic acid A mixture of 1 g (3 mmoles) of 1-(4-fluorophenyl)-6,7,8-trifluoro-1,4-dihydro-4-oxo-3-quinolinecarboxylic acid, 0.98 g (4.5 mmoles) of 3-methyl-3-trifluoroacetamidoazetidine hydrochloride and 0.6 g (6 mmoles) of triethylamine is heated under reflux for 3 hours in 10 ml of pyridine.

The mixture is evaporated under vacuum, water is added, and the mixture is acidified with acetic acid and filtered. After washing with water, 1.25 g (84.5%) of 1-(4-fluorophenyl)-6,8-difluoro-7-(3-amino-3-trifluoroacetamido-1-azetidinyl)-1,4-dihydro-4-oxo-3-quinolinecarboxylic acid are obtained, melting at 198°-203° C.

Spectroscopic data:

$^1$H NMR, $\delta$, [DMSO-6d, TFA]: 1.45 (s, 3H); 4.35 (m, 4H); 7.0-8 0 (m, 5H); 8.45 (s, 1H); 9.8 (s, 1H).
IR(KBr): 3400, 1734, 1701, 1627, 1489 cm$^{-1}$.

EXAMPLE 20

Preparation of 1-(4-fluorophenyl)-6,8-difluoro-7-(3-amino-3-methyl-1-azetidinyl)-1,4-dihydro-4-oxo-3-quinolinecarboxylic acid A solution of 1.25 g (2.5 mmoles) of 1-(4-fluorophenyl)-6,8-difluoro-7-(3-amino-3-trifluoroacetamido-1-azetidinyl)-1,4-dihydro-4-oxo-3-quinolinecarboxylic acid (example 19), in 8 ml of 1N sodium hydroxide and 10 ml of water is heated under reflux for 3 hours. It is cooled, filtered, and acetic acid is added. After filtering and washing with water and cold ethanol, 0.8 g (72%) of 1-(4-fluorophenyl)-6,8-difluoro-7-(3-amino-3-methyl-1-azetidinyl)-1,4-dihydro-4-oxo-3-quinolinecarboxylic acid are obtained, melting at 272°-7° C.

Spectroscopic data:

$^1$H NMR, $\delta$, [DMSO-6d]: 1.40 (s, 3H); 4.1 (broadened, 4H); 7.4 (m, 2H); 7.7 (m, 3H); 8.36 (s, 1H).
IR(KBr): 3400, 1728, 1626, 1466, 1325 cm$^{-1}$.

EXAMPLE 21

Preparation of 1-ethyl-6,8-difluoro-1,4-dihydro-4-oxo-7-(3-methyl-3-trifluoroacetamido-1-azetidinyl)-3-quinolinecarboxylic acid.

A solution of 1.1 g (4 mmoles) of 1-ethyl-6,7,8-trifluoro-1,4-dihydro-4-oxo-3-quinolinecarboxylic acid, 1.32 g (6 mmoles) of 3-methyl-3-trifluoroacetamidoazetidine hydrochloride and 0.8 g (8 mmoles) of triethylamine in 10 ml of pyridine is heated under reflux for 3 hours. Cooling, filtering and washing with water acidified with a little acetic acid yields 0.65 g (37%) of 1-ethyl-6,8-difluoro-1,4-dihydro-4-oxo-7-(3-methyl-3-trifluoroacetamido-1-azetidinyl)-3-quinolinecarboxylic acid, melting at 196°-210° C.

Spectroscopic data:

$^1$H NMR, $\delta$, [DMSO-6d, TFA]: 1.45 (m, 3H); 1.60 (s, 3H); 4.51 (m, 6H); 7.68 (d, 1H, J=13 Hz); 8.76 (s, 1H); 9.80 (m, 1H).
IR(KBr: 3400, 1724, 1707, 1629, 1497 cm$^{-1}$.

EXAMPLE 22

Preparation of 1-ethyl-6,8-difluoro-7-(3-amino-3-methyl-1-azetidinyl)-1,4-dihydro-4-oxo-3-quinolinecarboxylic acid A mixture of 0.65 g (1.5 mmoles) of 1-ethyl-6,8-difluoro-1,4-dihydro-4-oxo-7-(3-methyl-3-trifluoroacetamido-1-azetidinyl)-quinoline-3-carboxylic acid (example 21) 2 ml of 10% sodium hydroxide and 3 ml of ethanol is refluxed in 10 ml of water for 3 hours. It is filtered while hot, cooled, acidified with acetic acid, and filtered. After washing with water, 0.48 g (95%) of 1-ethyl-6,8-difluoro-7-(3-amino-3-methyl-1-azetidinyl)-1,4-dihydro-4-oxo-3-quinolinecarboxylic acid are obtained, melting at 293°-6° C.

Spectroscopic data:

$^1$H NMR, $\delta$, [DMSO-6d, TFA]: 1.41 (m, 3H); 1.60 (s, 3H); 4.4 (m, 6H); 7.76 (d, 1H, J=13 Hz); 8.43 (m, 2H); 8.77 (s, 1H).
IR(KBr): 3400, 1723, 1628, 1467 cm$^{-1}$.

EXAMPLE 23

Preparation of 1-cyclopropyl-6,8-difluoro-7-(3-amino-1-azetidinyl)-1,4-dihydro-4-oxo-3-quinolinecarboxylic acid.

A mixture of 1 g (3.2 mmoles) of ethyl 1-cyclopropyl-6,7,8-trifluoro-4-oxo-1,4-dihydro-quinoline-3-carboxylate, 0.98 g (4.8 mmoles) of 3-trifluoroacetamidoazetidine hydrochloride and 2 ml of triethylamine is heated in 15 ml of dimethyl sulphoxide for 4 hours at 80°-5° C. It is diluted with water and extracted with chloroform. The organic phase is washed with water and evaporated yielding 0.31 g (22% of ethyl 1-cyclopropyl-6,8-difluoro-1,4-dihydro-7-(3-trifluoroacetamido-1-azetidinyl)-4-oxo-3-quinolinecarboxylate which is then hydrolysed by heating a mixture of 0.1 g (0.22 mmoles) of this ester with 5 ml of 1N sodium hydroxide and 5 ml of ethanol. The mixture is cooled, evaporated and acidified with acetic acid. Filtering and washing with water yields 70 mg (96%) of 1-cyclopropyl-6,8-difluoro-7-(3-amino-1-azetidinyl)-1,4-dihydro-4-oxo-3-quinolinecarboxylic acid, melting at 214°-6° C.

Spectroscopic data:

$^1$H NMR, $\delta$, [DMSO-6d, TFA]: 1.0 (m, 4H); 3.40 (m, 1H); 3.9 (m, 1H); 4.45 (m, 4H); 7.5 (d, 1H, J=7 Hz); 8.3 (broadened, 2H); 8.5 (s, 1H).
IR(KBr): 3420, 2950, 1620, 1470, 1320 cm$^{-1}$.

EXAMPLE 24

Preparation of 1-cyclopropyl-6,8-difluoro-7-(3-trifluoroacetamidomethyl-3-methyl-1-azetidinyl)-1,4-dihydro-4oxo-3-quinolinecarboxylic acid A mixture of 1 g (3.5 mmoles) of 1-cyclopropyl-6,7,8-trifluoro-4-oxo-1,4-dihydroquinoline-3-carboxylic acid, 1.32 g (5.7 mmoles) of 3-methyl-3-trifluoroacetamidomethylazetidine hydrochloride and 2.3 g of triethylamine is heated under reflux in 12 ml of pyridine for 3 hours. The mixture is evaporated, water is added, and the product filtered. 1.6 g (100%) of 1-cyclopropyl-6,8-difluoro-7-(3-trifluoroacetamidomethyl-3-methyl-1-azetidinyl)-1,4-dihydro-4-oxo-3-quinolinecarboxylic acid are obtained, melting at 232°–7° C.

Spectroscopic data:

$^1$H NMR, δ, [DMSO-6d]: 1.25 (m, 7H); 3.5 (s, 2H); 4.20 (m, 5H); 7.62 (d, 1H, J=13 Hz); 8.56 (s, 1H); 9.27 (broadened, 1H)

IR(KBr): 3300, 1728, 1719, 1628, 1487, 1483 cm$^{-1}$

EXAMPLE 25

Preparation of 1-cyclopropyl-6,8-difluoro-7-(3-N-ethyltrifluoroacetamidomethyl-3-methyl-1-azetidinyl)-1,4-dihydro-4-oxo-3-quinolinecarboxylic acid A mixture of 1.5 g (5.3 mmoles) of 1-cyclopropyl-6,7,8-trifluoro-1,4-dihydro-4-oxo-3-quinolinecarboxylic acid, 2.1 g (8 mmoles) of 3-methyl-3-(N'-ethyl-trifluoroacetamidomethyl) azetidine hydrochloride and 3.3 g of triethylamine is heated under reflux for 3 hours in 15 ml of pyridine, it is evaporated, water is added, the product filtered and washed with water and ethanol. 1.8 g (70%) of 1-cyclopropyl-6,8-difluoro-7-(3-N'-ethyl-trifluoroacetamidomethyl-3-methyl-1-azetidinyl)-1,4-dihydro-4-oxo-3-quinolinecarboxylic acid are obtained, melting at 210°–2° C.

Spectroscopic data:

$^1$NMR, δ, [DMSO-6d,]: 1.25 (m, 10H); 3.48 (q, 2H, J=7 Hz); 3.72 (s, 2H); 4.18 (m, 5H); 7.67 (d, 1H, J=13 Hz); 8.58 (s, 1H).

IR(KBr): 1725, 1701, 1627, 1530, 1470 cm$^{-1}$.

EXAMPLE 26

Preparation of 1-cyclopropyl-6,8-difluoro-1,4-dihydro-4-oxo-7-(3-aminomethyl-3-methyl-1-azetidinyl)-3-quinolinecarboxylic acid A solution of 1.5 g (3.3 mmoles) of 1-cyclopropyl-6,8-difluoro-7-(3-trifluoroacetamidomethyl-3-methyl-1-azetidinyl)-1,4-dihydro-4-oxo-3-quinolinecarboxylic acid (example 24), 15 ml of 1N sodium hydroxide and 6 ml of ethanol are heated under reflux for 3 hours, and evaporated under vacuum. Acetic acid is added, and the product filtered and washed with water. 0.88 g (74%) of 1-cyclopropyl-6,8-difluoro-1,4-dihydro-4-oxo-7-(3-aminomethyl-3-methyl-1-azetidinyl)-3-quinolinecarboxylic acid are obtained, melting at 268°–70° C.

Spectroscopic data:

$^1$H NMR, δ, [DMSO-6d,]: 1.16 (d, 4H, J=6 2 Hz); 1.28 (s, 3H); 2.74 (s, 2H); 4.1 (m, 5H); 7.65 (d, 1H, J=13 Hz); 8.55 (s, 1H).

IR(KBr): 3400, 1725, 1627, 1465, 1455, 1322 cm$^{-1}$.

EXAMPLE 27

Preparation of 1-cyclopropyl-6,8-difluoro-7-(3-ethylaminomethyl-3-methyl-1-azetidinyl)-1,4-dihydro-4-oxo-3-quinolinecarboxylic acid, A solution of 1.7 g (3.5 mmoles) of 1-cyclopropyl-6,8-difluoro-7-(3-N'-ethyl-trifluoroacetamidomethyl-3-methyl-1-azetidinyl)-1,4-dihydro-4-oxo-3-quinolinecarboxylic acid (example 25), 15 ml of 1N sodium hydroxide and 6 ml of ethanol are heated under reflux for 3 hours, and evaporated under vacuum. The mixture is cooled, acetic acid is added, the product is filtered and washed with water. 1.08 g (80%) of 1-cyclopropyl-6,8-difluoro-7-(3-ethylaminomethyl-3-methyl-1-azetidinyl)-1,4-dihydro-4-oxo-3-quinolinecarboxylic acid are obtained, melting at 250°–5° C.

Spectroscopic data:

$^1$H NMR, δ, [DMSO-d$_6$, ]: 1.1 (m, 7H); 1.31 (s, 3H); 2.7 (m, 4H); 4.1 (m, 5H); 7.63 (d, 1H, J=13 Hz); 8.55 (s, 1H).

IR(KBr): 3440, 1615, 1475, 1400, 1320 cm$^{-1}$.

EXAMPLE 28

Preparation of [S]-(−)-9-fluoro-3-methyl-7-oxo-2,3dihydro-7H-pyrido[1,2,3-de] [1,4] benzoxazine-10-(3-amino-3-methyl-1-azetidinyl)-6-carboxylic acid.

A mixture of 0.7 g (2.5 mmoles) of [S]-(−)-9,10-difluoro-3-methyl-7-oxo-2,3-dihydro-7H-pyrido [1,2,3-de] [1,4] benzoxazine-6-carboxylic acid, 1.1 g (5 mmoles) of 3-methyl-3-trifluoroacetamidoazetidine hydrochloride and 1 g (9.9 mmoles) of triethylamine is heated under reflux in 10 ml of pyridine for 6 hours. The mixture is evaporated under vacuum, diluted with water, acidified with acetic acid, filtered and the product washed with water and with a 50% aqueous solution of ethanol. 0.67 g (60%) of [S]-(−)-9-fluoro-3-methyl-7-oxo-2,3-dihydro-7H-pyrido [1,2,3-de] [1,4] benzoxazine-10-(3-methyl-3-trifluoroacetamido-1-azetidinyl)-6-carboxylic acid are obtained, which is subsequently added to a solution of 2 ml of ethanol in 9 ml of 1N sodium hydroxide. This mixture is heated to reflux for 3 hours, filtered, evaporated, and water and acetic acid are added. The product is filtered, washed with water and 0.37 g (70%) of [S]-(−)-9-fluoro-3-methyl-7-oxo-2,3-dihydro-7H-pyrido [1,2,3-de][1,4]benzoxazine-10-(3-amino-3-methyl-1-azetidinyl)-6-carboxylic acid are obtained melting at >300° C.

Optical rotation: [α]$_D^{23}$ 3 [con. (%) solvent] = −83.1 (c=0.41; 0.5N; NaOH)

Spectroscopic data:

$^1$H NMR, δ, [DMSO-d$_6$, TFA]: 1.45 (d, 3H, J=6 Hz); 1.45 (s, 3H); 4.28 (m, 6H); 4.72 (m, 1H); 7.47 (d, 1H, J=13 4 Hz); 8.66 (s, 1H)

IR(KBr): 3493, 1706, 1623, 1473 cm$^{-1}$.

EXAMPLE 29

Preparation of R-(+)-9-fluoro-3-methyl-7-oxo-2,3-dihydro-7H-pyrido [1,2,3-de][1,4]benzoxazine-10-(3-amino-3-methyl-1-azetidinyl)-6-carboxylic acid The same method is followed as was described for the preparation of the S enantiomer (Example 28), but starting from [R]-(+)-9,10-difluoro-3-methyl-7-oxo-2,3-dihydro-7H-pyrido[1,2,3-de][1,4]benzoxazine-6-carboxylic acid. 0.28 g (53%) of R-(+)-9-fluoro-3-methyl-7-oxo-2,3-dihydro-7H-pyrido[1,2,3-de][1,4]benzoxazine-10-(3-amino-3-methyl-1-azetidinyl)-6-carboxylic acid are obtained, melting at >300° C.

Optical rotation: [α]$_D^{23}$ [con. (%) solvent] = +82.2 (c=0.43; 0.5N; NaOH)

Spectroscopic data $^1$H NMR, δ, [DMSO-d$_6$, TFA]: 1.48 (d, 3H, J=6 Hz); 1.43 (s, 3H); 4.3 (m, 6H); 4.69 (m, 1H); 7.50 (d, 1H, J=13.5 Hz); 8.62 (s, 1H)

IR(KBr): 3500, 1708, 1620, 1472 cm$^{-1}$.

EXAMPLE 30

Preparation of 1-cyclopropyl-6-fluoro-7-(3-trifluoroacetamidomethyl-3-methyl-1-azetidinyl)-1,4-dihydro-4-oxo-3-quinolinecarboxylic acid A mixture of 0.7 g (2.6 mmoles) of 1-cyclopropyl-6,7-difluoro-4-oxo-1,4-dihydro-quinoline-3-carboxylic acid, 0.92 g (3.96 mmoles) of 3-methyl-3-trifluoroacetamidomethylazetidine hydrochloride and 1.6 g of triethylamine are heated under reflux for 2 hours in 12 ml of pyridine. The mixture is evaporated, water is added, the product is filtered, and 1.05 g (90%) of 1-cyclopropyl-6-fluoro-7-(3-trifluoroacetamidomethyl-3-methyl-1-azetidinyl)-1,4-dihydro-4-oxo-3-quinolinecarboxylic acid are obtained, melting at 265°–72° C.

Spectroscopic data $^1$H NMR, δ, [DMSO-6d,]: 1.28 (m, 7H); 3.53 (s, 2H); 4.0 (m, 5H); 6.85 (d, 1H, J=6.9 Hz); 7.76 (d, 1H, J=12.9 Hz); 8.56 (s, 1H)

IR(KBr): 3300, 1725, 1720, 1630, 1487, 1517, 1474 cm$^{-1}$

EXAMPLE 31

Preparation of 1-cyclopropyl-6-fluoro-7-(3-N'-ethyl-trifluoroacetamidomethyl-3-methyl-1-azetidinyl)-1,4-dihydro-4-oxo-3-quinolinecarboxylic acid A mixture of 0.7 g (2.6 mmoles) of 1-cyclopropyl-6,7-difluoro-1,4-dihydro-4-oxo-3-quinolinecarboxylic acid, 1.04 g (3.9 mmoles) of 3-methyl-3-(N'-ethyl-trifluoroacetamidomethyl)-azetidine hydrochloride and 1.6 g of triethylamine are heated under reflux in 12 ml of pyridine, evaporated, water is added, the product is filtered and washed with water. 0.78 g (63%) of 1-cyclopropyl-6-fluoro-7-(3-N'-ethyl-trifluoroacetamidomethyl-3-methyl-1-azetidinyl)-1,4-dihydro-4-oxo-3-quinolinecarboxylic acid are obtained, melting at 230°–6° C.

Spectroscopic data $^1$H NMR, δ, [DMSO-6d,]: 1.25 (m, 10H); 3.48 (q, 2H, J=6.5 Hz); 3.72 (s, 2H); 4.04 (m, 5H); 7.90 (d, 1H, J=8 Hz); 7.76 (d, 1H, J=12 8 Hz); 8.56 (s, 1H).

IR(KBr): 1721, 1701, 1631, 1519, 1474, 1450 cm$^{-1}$.

EXAMPLE 32

Preparation of 1-cyclopropyl-6-fluoro-1,4-dihydro-4-oxo-7-(3-aminomethyl-3-methyl-1-azetidinyl)-quinoline-3-carboxylic acid A solution of 1.05 g (2.38 mmoles) of 1-cyclopropyl-6-fluoro-7-(3-trifluoroacetamidomethyl)-3-methyl-1-azetidinyl)-1,4-dihydro-4-oxo-3-quinolinecarboxylic acid (Example 30), in 15 ml of 1N sodium hydroxide and 6 ml of ethanol is heated to reflux for 3 hours, and evaporated under vacuum. Acetic acid is added, the product is filtered and washed with water, and 0.7 g (85%) of 1-cyclopropyl-6-fluoro-1,4-dihydro-4-oxo-7-(3-aminomethyl-3-methyl-1-azetidinyl)-3-quinolinecarboxylic acid, melting at 274°–9° C., are obtained.

Spectroscopic data $^1$H NMR, δ, [DMSO-6d,]: 1.24 (m, 7H); 2.76 (s, 2H); 3.90 (m, 5H); 6.84 (d, 1H, J=7.6 Hz); 7.75 (d, 1H, J=12.9 Hz); 8.55 (s, 1H).

IR(KBr): 3400, 1721, 1631, 1520, 1470, 1395 cm$^{-1}$.

EXAMPLE 33

Preparation of 1-cyclopropyl-6-fluoro-7-(3-ethylaminomethyl-3-methyl-1-azetidinyl)-1,4-dihydro-4-oxo-3-quinolinecarboxylic acid A solution of 0.78 g (3.5 mmoles) of 1-cyclopropyl-6-fluoro-7-(3-trifluoroacetamidoethylaminomethyl-3-methyl-1-azetidinyl)-1,4-dihydro-4-oxo-3-quinolinecarboxylic acid (example 31) is heated under reflux for 3 hours in 15 ml of sodium hydroxyde 1N and 6 ml of ethanol then evaporated under vacuum. The mixture is cooled, acetic acid is added, filtrated and washed with water to obtain 0.4 g (65%) of 1-cyclopropyl-6-fluoro-7-(-3-ethylaminomethyl-3-methyl-1-azetidinyl)-1,4-dihydro-4-oxo-3-quinolinecarboxylic acid melting at 221°–6° C.

Spectroscopic data $^1$H NMR, δ, [DMSO-d$_6$,]: 1.15 (m, 10H); 2.68 (m, 4H); 3.9 (m, 5H); 6.84 (d, 1H, J=7.6 Hz); 7.75 (d, 1H, J=12 8 Hz); 8.55 (s, 1H).

IR(KBr): 3420, 1629, 1619, 1578, 1517, 1484, 1402 cm$^{-1}$.

EXAMPLE 34

Preparation of 1-(2,4-difluorophenyl)-6,8-difluoro-7-(3-methyl-3-trifluoroacetamido-1-azetidinyl)-1,4-dihydro-4-oxo-3-quinolinecarboxylic acid A mixture of 0.8 g (2.3 mmoles) of 1-(2,4-difluorophenyl)-6,7,8-trifluoro-1,4-dihydro-4-oxo-3-quinolinecarboxylic acid, 0.8 g (3.7 mmoles) of 3-methyl-3-trifluoroacetamidozaetidine hydrochloride and 0.6 g (6 mmoles) of triethylamine is heated under reflux in 15 ml of pyridine.

The mixture is evaporated under vacuum, water is added, the mixture acidified with acetic acid, and the product is filtered and washed with water. 1.10 g (57%) of 1-(2,4-difluorophenyl)-6,8-difluoro-7-(3-amino-3-trifluoroacetamido-1-azetidinyl)-1,4-dihydro-4-oxo-3-quinolinecarboxylic acid are obtained, melting at 190°–6° C.

Spectroscopic data $^1$H NMR, δ, [DMSO-6d, TFA]: 1.54 (s, 3H); 4.4 (m, 4H); 7.0–8.0 (m, 4H); 8.60 (s, 1H); 9.7 (s, 1H).

IR(KBr): 3400, 1720, 1711, 1626, 1459 cm$^{-1}$.

EXAMPLE 35

Preparation of 1-(2,4-difluorophenyl)-6,8-difluoro-7-(3-amino-3-methyl-1-azetidinyl)-1,4-dihydro-4-oxo-3-quinolinecarboxylic acid A solution of 1.1 g (2.1 mmoles) of 1-(2,4-difluorophenyl)-6,8-difluoro-7-(3-methyl-3-trifluoroacetamido-1-azetidinyl)-1,4-dihydro-4-oxo-3-quinolinecarboxylic acid (example 34), 4 ml of 10% sodium hydroxide, 5 ml of ethanol and 25 ml of water is heated under reflux for 3 hours. It is cooled, filtered, acetic acid is added and the product filtered and washed with water and cold ethanol. 0.2 g (22%) of 1-(2,4-difluorophenyl)-6,8-difluoro-7-(3-amino-3-methyl-1-azetidinyl)-1,4-dihydro-4-oxo-3-quinolinecarboxylic acid are obtained, melting at 185°–6° C.

Spectroscopic data $^1$H NMR, δ, [DMSO-6d, TFA]: 1.54 (s, 3H); 4.31 (broadened, 4H); 7.3–8.1 (m, 4H); 8.48 (broadened, 2H); 8.62 (s, 1H).

IR(KBr): 3410, 1729, 1625, 1510, 1461 cm$^{-1}$.

EXAMPLE 36

Preparation of 1-ethyl-6-fluoro-7-(3-amino-3-methyl-1-azetidinyl)-1,4-dihydro-4-oxo-3-quinolinecarboxylic acid.

A mixture of 0.8 g (3.16 mmoles) of 1-ethyl-6,7-difluoro-4-oxo-1,4-dihydro-quinoline-3-carboxylic acid, 1.5 g (6.8 mmoles) of 3-methyl-3-trifluoroacetamidoazetidine hydrochloride and 1 g (10 mmoles) of triethylamine is heated under reflux in 15 ml of pryidine.

The mixture is diluted with water and extracted with chloroform. The organic phase is washed with water and evaporated to obtain 1.0 g (76%) of 1-ethyl-6-fluoro-4-oxo-1,4-dihydro-7-(3-methyl-3-trifluoroacetamido-1-azetidinyl)-4-oxo-3-quinolinecarboxylic acid which is subsequently hydrolysed by heating a mixture of 1.0 g (2.4 mmoles) of this acid with 3 ml of 10% sodium hydroxide and 20 ml of water under reflux for 3 hours. The mixture is cooled and acidified with acetic acid. The product is filtered and washed with water to obtain 370 mg (48%) of 1-ethyl-6-fluoro-7-(3-methyl-3-amino-1-azetidinyl)-1,4-dihydro-4-oxo-3-quinolinecarboxylic acid, melting at 280°–3° C.

Spectroscopic data $^1$H NMR, δ, [DMSO-6d]: 1.46 (m, 6H); 4.00 (m, 4H); 4.50 (m, 2H); 0.6 (d, 1H, J=7 8 Hz); 7.82 (d, 1H, J=12.9 Hz); 8.87 (s, 1H).

IR(KBr): 3420, 1709, 1631, 1430, 1360 cm$^{-1}$.

EXAMPLE 37

Preparation of 1-(2-fluoroethyl)-6-fluoro-7-(3-methyl-3-amino-1-azetidinyl)-1,4-dihydro-4-oxo-3-quinolinecarboxylic acid.

A mixture of 0.8 g (2.5 mmoles) of 1-(2-fluoroethyl)-6,7-difluoro-1,4-dihydro-4-oxo-3-quinolinecarboxylic acid, 1.37 g (6.3 mmoles) of 3-methyl-3-trifluoroacetamidoazetidine hydrochloride and 1.1 g (10 mmoles) of triethylamine is heated under reflux in 10 ml of pyridine.

The mixture is evaporated under vacuum, and extracted with methylene chloride. After washing with water 1.2 g (99%) of 1-(2-fluoroethyl)-6-fluoro-7-(3-methyl-3-trifluoroacetamido-1-azetidinyl)-1,4-dihydro-4-oxo-3-quinolinecarboxylic acid are obtained, melting at 225°–8° C.

This product is hydrolysed by heating a solution of 1.1 g (2.3 mmoles) of this trifluoroacetamide in 25 ml of water to which have been added 3 ml of 10% sodium hydroxide under reflux for 2 hours. The solution is filtered while hot, acidified with acetic acid, the product filtered, washed with water and ethanol, and 0.3 g (34%) of 1-(2-fluoroethyl)-6-fluoro-7-(3-methyl-3-amino-1-azetidinyl)-1,4-dihydro-4-oxo-3-quinolinecarboxylic acid are obtained, melting at 265°–70° C.

Spectroscopic data $^1$H NMR, δ, [DMSO-6d]: 1.47 (s, 3H); 4.04 (m, 4H); 4.65 (m, 2H); 6.02 (s, 2H); 6.60 (d, 1H, J=7,3 Hz); 7.31 (d, 1H, J=12.9 Hz) 8.78 (s, 1H)

IR(KBr): 3480, 1719, 1632, 1463 cm$^{-1}$.

EXAMPLE 38

Preparation of 1-(2,4-difluorophenyl)-6-fluoro-7-(3-methyl-3-amino-1-azetidinyl)-1,4-dihydro-4-oxo-3-quinolinecarboxylic acid A mixture of 1.3 g (6 mmoles) of 3-methyl-3-trifluoroacetamidozaetidine hydrochloride, 0.8 g (2.4 mmoles) of 1-(2,4-difluorophenyl)-6,7-difluoro-1,4-dihydro-4-oxo-3-quinolinecarboxylic acid and 0.8 g (8 mmoles) of triethylamine is heated under reflux in 20 ml of pyridine for 2 hours. The mixture is evaporated, extracted with methylene chloride to obtain 1.1 g (92%) of 1-(2,4-difluorophenyl)-6-fluoro-7-(3-methyl-3-trifluoroacetamido-1-azetidinyl)-1,4-dihydro-4-oxo-3-quinolinecarboxylic acid which is subsequently hydrolysed by adding it to a solution of 3 ml of 10% sodium hydroxide in 20 ml of water and refluxing for 2 hours. The solution is filtered while hot, acidified with acetic acid, filtered and the product washed with water and ethanol. 0.27 g (30%) of 1-(2,4-difluorophenyl)-6-fluoro-7-(3-methyl-3-amino-1-azetidinyl)-1,4-dihydro-4-oxo-3-quinolinecarboxylic acid are obtained, melting at 210°–6° C.

Spectroscopic data $^1$H NMR, δ, [DMSO-6d, TFA]; 1.56 (s, 3H); 4.00 (m, 4H); 6.72 (d, 1H, J=7.1 Hz); 7.3–8.1 (m, 4H); 8.44 (broadened, 2H) 8.70 (s, 1H).

IR(KBr): 3400, 1725, 1630, 1509, 1474 cm$^{-1}$.

EXAMPLE 39

Preparation of 1-cyclopropyl-6,8-difluoro-1,4-dihydro-4-oxo-7-(3-methyl-3-N,N-dimethylamino-1-azetidinyl)-3-quinolinecarboxylic acid.

A solution of 1.5 g (5.3 mmoles) of 1-cyclopropyl-6,7,8-trifluoro-1,4-dihydro-4-oxo-3-quinolinecarboxylic acid, 1.5 g (8 mmoles) of 3-methyl-3-N,N-dimethylaminoazetidine hydrochloride and 3.3 g (33 mmoles) of triethylamine in 15 ml of pyridine is heated under reflux for 3 hours. It is cooled, evaporated under vacuum, water is added, the mixture is made alkaline with 10% sodium hydroxide solution, filtered then acidified with acetic acid. A precipitate is obtained which is made slightly alkaline with ammonia. The product is heated to evaporate excess ammonia, yielding 1.85 g (92%) of 1-cyclopropyl-6,8-difluoro-1,4-dihydro-4-oxo-7-(3-methyl-3-N,N-dimethylamino-1-azetidinyl)-3-quinolinecarboxylic acid melting at 280°–4° C.

Spectroscopic data $^1$H NMR, δ, [DMSO-6d, TFA]: 1.19 (d, 4H, J=6.5 Hz); 1.71 (s, 3H); 2.82 (s, 6H); 4.03 (m, 1H); 4.52 (m, 4H); 7.76 (dd, 1H, J=12 8 Hz, J'=1.8 Hz); 8.62 (s, 1H).

IR(KBr): 1723, 1626, 1552, 1492, 1451 cm$^{-1}$.

EXAMPLE 40

Preparation of 1-cyclopropyl-6-fluoro-7-(3-amino-3-methyl-1-azetidinyl)-1,4-dihydro-4-oxo-3-quinolinecarboxylic acid.

A mixture of 0.8 g (3.0 mmoles) of 1-cyclopropyl-6,7-difluoro-4-oxo-1,4-dihydro-quinoline-3-carboxylic acid, 1.7 g (7.8 mmoles) of 3-methyl-3-trifluoroacetamidomethylazetidine hydrochloride and 1.4 g of triethylamine is heated under reflux in 15 ml of pyridine. The mixture is evaporated, water is added and the product filtered yielding 0.55 g (42%) of 1-cyclopropyl-6-fluoro-7-(3-trifluoroacetamido-3-methyl-1-azetidinyl)-1,4-dihydro-4-oxo-3-quinolinecarboxylic acid, which is subsequently hydrolysed by heating it under reflux with a solution of 3 ml of 10% sodium hydroxide in 10 ml of water for 2 hours. The volume is reduced by half, a few drops of acetic acid are added, and the product is filtered and washed with water. This yields 0.36 g (84%) of 1-cyclopropyl-6-fluoro-7-(3-amino-3-methyl-1-azetidinyl)-1,4-dihydro-4-oxo-3-quinolinecarboxylic acid, melting at 293°–5° C.

Spectroscopic data $^1$H NMR, δ, (DMSO-6d]: 1.22 (m, 4H); 1.45 (s, 3H); 3.69 (m, 1H); 4.0 (m, 4H); 6.85 (d, 1H, J=7.8 Hz) 7.75 (d, 1H, J=12 9 Hz); 8.55 (s, 1H).

IR(KBr): 3340, 1722, 1630, 1528, 1471 cm$^{-1}$.

EXAMPLE 41

Preparation of 1-(2-fluoroethyl)-6,8-difluoro-7-(3-amino-3-methyl-1-azetidinyl)-1,4-dihydro-4-oxo-3-quinolinecarboxylic acid A mixture of 0.8 g (2.8 mmoles) of 1-(2-fluoroethyl)-6,7,8-trifluoro-4-oxo-1,4-dihydro-quinoline-3-carboxylic acid, 1.3 g (6 mmoles) of 3-methyl-3-trifluoroacetamidoazetidine hydrochloride and 1 g (10 mmoles) of triethylamine is heated under reflux in 15 ml of pyridine for 2 hours.

The mixture is evaporated under vacuum and extracted with methylene chloride. Filtration and evaporation yield 1.2 g (95%) of 1-(2-fluoroethyl)-6,8-difluoro-1,4-dihydro-7-(3-methyl-3-trifluoroacetamido-1-azetidinyl)-4-oxo-3-quinolinecarboxylic acid melting at 205°–15° C. This product is subsequently hydrolysed by heating a mixture of 1.0 g (2.0 mmoles) of this acid with 3 ml of 10% sodium hydroxide and 20 ml of water under reflux for 3 hours. The mixture is cooled and acidified with acetic acid and filtered. The product is washed with water yielding 380 mg (48%) of 1-(2-fluoroethyl)-6,8-difluoro-7-(3-methyl-3-amino-1-azetidinyl)-1,4-dihydro-4-oxo-3-quinolinecarboxylic acid, melting at 281°–4° C.

Spectroscopic data $^1$H NMR, δ, [DMSO-6d]: 1.41 (s, 3H), 4.17 (m, 4H); 4.62 (m, 2H); 5.04 (m, 2H); 7.66 (d, 1H, J=12.3 Hz); 8.73 (s, 1H).

IR(KBr): 3410, 1725, 1629, 1614, 1474 cm$^{-1}$.

EXAMPLE 42

Preparation of 1-(4-fluorophenyl)-6-fluoro-7-(3-amino-3-methyl-1-azetidinyl)-1,4-dihydro-4-oxo-3-quinolinecarboxylic acid A mixture of 0.8 g (2.5 mmoles) of 1-(4-fluorophenyl)-6,7-difluoro-1,4-dihydro-4-oxo-3-quinolinecarboxylic acid, 1.3 g (6 mmoles) of 3-methyl-3-trifluoroacetamidoazetidine hydrochloride and 1 g of triethylamine is heated under reflux in 20 ml of pyridine for 3 hours. The mixture is evaporated, and extracted with methylene chloride. Filtration and evaporation yield 1.1 g of 1-(4-fluorophenyl)-6-fluoro-7-(3-trifluoroacetamido-3-methyl-1-azetidinyl)-1,4-dihydro-4-oxo-3-quinolinecarboxylic acid, melting at 146°–151° C., which is subsequently hydrolysed in a manner similar to that in example 41, to obtain 0.5 g (56%) of 1-(4-fluorophenyl)-6-fluoro-7-(3-amino-3-methyl-1-azetidinyl)-1,4-dihydro-4-oxo-3-quinolinecarboxylic acid, melting at 270°–6° C.

Spectroscopic data $^1$H NMR, δ, [DMSO-6d]: 1.35 (s, 3H); 2.9 (m, 2H); 3.76 (m, 4H); 5.70 (d, 1H, J=7.9 Hz); 7.2–7.9 (m, 5H); 8.48 (s, 1H).

IR(KBr): 3420, 1720, 1630, 1505 cm$^{-1}$.

EXAMPLE 43

Preparation of 1-cyclopropyl-6,8-difluoro-7-(3-dimethylamino-1-azetidinyl)-1,4-dihydro-4-oxo-3-quinolinecarboxylic acid A mixture of 1.5 g (5.3 mmoles) of 1-cyclopropyl-6,7,8-trifluoro-1,4-dihydro-4-oxo-3-quinolinecarboxylic acid, 1.4 g (8 mmoles) of 3-dimethylaminoazetidine dihydrochloride and 6.6 g of triethylamine is heated under reflux in 15 ml of pryidine for 3 hours. It is evaporated, water is added and the resulting mixture is made alkaline with 1N sodium hydroxide, heated, filtered while hot, acidified with acetic acid, and filtered. After washing with water, 1.7 g (88%) of 1-cyclopropyl-6,8-difluoro-7-(3-dimethylamino-1-azetidinyl)-1,4-dihydro-4-oxo-3-quinolinecarboxylic acid are obtained, melting at 256°–60° C.

Spectroscopic data $^1$H NMR, δ, [DMSO-6d]; 1.18 (d, 4H, J=5.7 Hz); 2.16 (s, 6H); 3.28 (m, 1H); 4.24 (m, 5H); 7.68 (d, 1H, J=12.9 Hz); 8.57 (s, 1H).

IR(KBr): 1718, 1629, 1528, 1459, 1439 cm$^{-1}$.

EXAMPLE 44

Preparation of 1-cyclopropyl-6-fluoro-7-(3-dimethylamino-1-azetidinyl)-1,4-dihydro-4-oxo-3-quinolinecarboxylic acid.

A mixture of 0.25 g (1.32 mmoles) of 1-cyclopropyl-6,7-difluoro-1,4-dihydro-4-oxo-3-quinolinecarboxylic acid, 0.34 g (12 mmoles) of 3-dimethylaminoazetidine dihydrochloride and 3.3 g (33 mmoles) of triethylamine is heated under reflux in 10 ml of pryidine for 2 hours. The mixture is evaporated under vacuum, water is added and the resulting mixture made alkaline with 1N sodium hydroxide, heated, filtered while hot, acidified with acetic acid and filtered again. After washing with water, 0.4 g (88%) of 1-cyclopropyl-6-fluoro-7-(3-dimethylamino-1-azetidinyl)-1,4-dihydro-4-oxo-3-quinolinecarboxylic acid are obtained, melting at 255°–61° C.

Spectroscopic data $^1$H NMR, δ, [DMSO-6d]; 1.21 (m, 4H); 2.18 (s, 6H); 3.34 (m, 1H); 3.70 (m, 1H); 4.14 (m, 4H); 6.88 (d, 1H, J=7.5 Hz); 7.76 (d, 1H, J=12.9 Hz); 8.56 (s, 1H).

EXAMPLE 45

Preparation of 1-cyclopropyl-6,8-difluoro-7-(3-amino-3-methyl-1-azetidinyl)-1,4-dihydro-4-oxo-3-quinolinecarboxylic acid hydrochloride 0.5 g (1.4 mmoles) of 1-cyclopropyl-6,8-difluoro-7-(3-amino-3-methyl-1-azetidinyl)-1,4-dihydro-4-oxo-3-quinolinecarboxylic acid are suspended in 10 ml of methanol, and to this is added an excess of a methanolic solution of gaseous hydrogen chloride. The mixture is agitated for 30 minutes, and ethyl ether and petroleum ether are added. After filtering, washing with ethyl ether and drying by heating, 0.45 g (82%) of 1-cyclopropyl-6,8-difluoro-7-(3-amino-3-methyl-1-azetidinyl)-1,4-dihydro-4-oxo-3-quinolinecarboxylic acid hydrochloride are obtained, melting at 249°–250° C.

Spectroscopic data $^1$H NMR, δ, [DMSO-6d]; 1.20 m, 4H); 1.65 (m, 3H); 3.29 (broadened, H$_2$O) 4.05 (m, 1H); 4.46 (m, 4H); 7.76 (d, 1H, J=12.8 Hz); 8.61 (s, 1H) 8.72 (broadened, 2H).

IR(KBr): 3431, 1719, 1629, 1531, 1462, 1333 cm$^{-1}$.

EXAMPLE 46

Preparation of the sodium salt of 1-cyclopropyl-6,8-difluoro-7-(3-amino-3-methyl-1-azetidinyl)-1,4-dihydro-4-oxo-3-quinolinecarboxylic acid.

95 mg (0.27 mmoles) of 1-cyclopropyl-6,8-difluoro-7-(3-amino-3-methyl-1-azetidinyl)-1,4-dihydro-4-oxo-3-quinolinecarboxylic acid are added to a solution of 22.8 mg (0.27 mmoles) of sodium bicarbonate in 5 ml of water, and vigorously agitated; a few drops of ethanol are added and the mixture is heated to 80° C. for 18 hours then evaporated. Ethanol is added and the mixture filtered. After washing with ethanol, 62 mg (63%) of the sodium salt of 1-cyclopropyl-6,8-difluoro-7-(3-amino-3-methyl-1-azetidinyl)-1,4-dihydro-4-oxo-3-quinolinecarboxylic acid are obtained, melting at >300° C.

Spectroscopic data $^1$H NMR, δ, [D$_2$O]; 0.89 (m, 2H); 0.98 (m, 2H); 1.29 (s, 3H); 3.72 (m, 1H); 3.94 (m, 2H); 4.04 (m, 2H); 7.44 (dd, 1H, J=12.93 Hz, J'=1.45 Hz); 8.23 (s, 1H).
IR(KBr): 3400, 16230, 1462, 1400, cm$^{-1}$.

EXAMPLE 47

Preparation of 1-cyclopropyl-6,8-difluoro-7-3-methylamino-1-azetidinyl)-1,4-dihydro-4-oxo-3-quinolinecarboxylic acid A mixture of 0.85 g (3.0 mmoles) of 1-cyclopropyl 6,7,8-trifluoro-4-oxo-1,4-dihydro-3-quinolinecarboxylic acid 1.3 g (6 mmoles) of 3-methyl-3-trifluoroacetamidoazetidine hydrochloride and 0.8 g (8 mmoles) of triethylamine in 15 ml of pyridine is refluxed for 2 hours.

The mixture is evaporated under vacuum and acidified with aqueous acetic acid to obtain (1.1 g of 1-cyclopropyl-6,8-difluoro-4-oxo-1,4-dihydro-7-(3-methyl-3-trifluoroacetamido-1-azetidinyl)-4-oxo-3-quinolinecarboxylic and which is subsequently hydrolysed by heating a mixture of 1.0 g (2.0 mmoles) of this acid with 3 ml of sodium hydroxyle and 20 ml of water under reflux for 3 hours. The solution is cooled and acidified with acetic acid, filtrated, washed with water to obtain 0.6 g (48%) of 1-cyclopropyl-6,8 difluoro-7-(3-methylamino-1-azetidinyl)-1,4-dihydro-4-oxo-3-quinolinecarboxylic and melting at 270°-2° C.

Spectroscopic data $^1$H RMN, δ, [DMSO-6d]: 1,17 (d, 4H, J-6,5 Hz); 2,31 (s, 3H); 3,66 (m, 1H); 4,12 (m, 3H); 4,52 (m, 2H); 7,66 (dd, 1H, J=12,3 Hz, J'=1,7 Hz); 8,58 (s, 1H).
IR(KBr): 3468, 3387, 2912, 1718, 1629, 1617, 1472 cm$^{-1}$.

EXAMPLE 48

Preparation of 1-cyclopropyl-6-fluoro-7-(3-methylamino-1-azetidinyl)-1,4-dihydro-4-oxo-3-quinolinecarboxylic acid A mixture of 0.5 g (2.0 mmoles) of 1-cyclopropyl-6,7-difluoro-1,4-dihydro-4-oxo-3-quinolinecarboxylic acid, 1.2 g (6 mmoles) of 3-methyl-3-trifluoroacetamidoazetidine hydrochloride and 0.8 g of triethylamine is heated under refluxed in 20 ml of pyridine for 3 hours. The mixture is evaporated and water is added to obtain 0.7 g of 1-cyclopropyl-6-fluoro-7-(3-methyl-3-trifluoromethylacetamido-1-azetidinyl)-1,4-dihydro-4-oxo-3-quinolinecarboxylic acid which is subsequently hydrolysed with the same method as was described in the example 47 to obtain 250 mg of 1-cyclopropyl-6-fluoro-7-(3-methylamino-1-azetidinyl)-1,4-dihydro-4-oxo-3-quinolinecarboxylic acid of melting point 245°-9° C.

Spectroscopic data $^1$H RMN, δ, [DMSO-6d]; 1,25 (m, 4H); 2,32 (s, 3H); 3,72 (m, 1H); 3,90 (m, 3H); 4,36 (m, 2H); 6,86 (d, 1H, J=7,9 Hz); 7,77 (d, 1H, J=12,9 Hz); 8,56 (s, 1H)
IR(KBr): 3468, 3387, 2912, 1718, 1629, 1515, 1480 cm$^{-1}$.

EXAMPLE 49

Preparation of 1-cyclopropyl-6-fluoro-7-(3-amino-1-azetidin-1,4-dihydro-4-oxo-3-quinolinecarboxylic acid.

A mixture of 1.2 g (4.53 mmoles) of 1-cyclopropyl 6,7-difluoro-1,4-dihydro-4oxo-3-quinolinecarboxylic acid, 1.3 g (9.05 mmoles) of 3-aminoazetidine hydrochloride and 0.5 ml of triethylamine heated in 15 ml of pyridine for 2 hours. The mixture is filtrated and washed with water and ethanol to obtain 0.83 g (58%) of 1-cyclopropyl-6-fluoro-7-(3-amino-1-azetidinyl)-1,4-dihydro-4-oxo-3-quinolinecarboxylic acid melting at 246°-7° C.

$^1$H RMN, δ, [DMSO-6d]; 1,28 (m, 4H); 3,87 (m, 4H); 4,40 (m, 2H); 6,60 (elargie, 2H); 6,86 (d, 1H, J=8 Hz); 7,77 (d, 1H, J=13 Hz); 8,56 (s, 1H).

The pharmacological antimicrobial activity of these compounds has been studied according to the information given hereinafter.

*Pharmacological antimicrobial activity* (G. L. Daquet and Y. A. Chabbect, Techniques en Bactériologie, Vol. 3, Flammarion Médecine-Sciences, Paris 1972 and W. B. Hugo and A. D. Rusell, Pharmaceutical Microbiology, Blackwell Scientific Publications, London (1977).

Culture medium and solvent

Antibiotic Agar N° 1 (Oxoid CM 327)
Tryptone-soya Broth (Oxoid CM 129)
Ringer physiological solution ¼ (Oxoid BR 52) Dextrose Agar (BBL-11165)
NaOH 0.1N

Microorganisms

"Bacillus subtilis" ATCC 6633
"Citrobacter freundii" ATCC 11606
"Enterobacter aerogenes" ATCC 15038
"Enterobacter cloacae" ATCC 23355
"Bacillus cereus" ATCC 1178
"Escherichia coli" ATCC 10799
"Escherichia coli" ATCC 23559
"Klebsiella pneumoniae" ATCC 10031
"Proteus Vulgaris" ATCC 8427
"Morg. morganii" ATC 8019
"Pseudomonas aeruginosa" ATCC 9721
"Pseudomonas aeruginosa" ATCC 10145
"Salmonella tiphymurium" ATCC 14028
"Salmonella tiphymurium" ATCC 6539
"Serratia marcescens" ATCC 13880
"Shigella flexnerii" ATCC 12022
"Staphylococcus epidermis ATCC 155-1
"Staphylococcus aureus" ATCC 25178
"Streptococcus faecalis" ATCC 10541

Preparation of the inocula

Each of the microorganisms is seeded in striae in tubes containing Antibiotic Agar No 1, and left to incubate at 37° C. for 20 hours. Then a culturing loop is taken and the microorganisms are seeded into a Tryptonesoya broth and incubated at 37° C. for 20 hours. The resulting culture is diluted with Ringer physiological solution in proportions of ¼, so as to obtain a standardised 10⁷-10⁹ cfu/ml suspension of each organism.

Preparation of the medium containing the derivatives of general formula I

A solution of 1000 μg/ml of each product in 0.1N NaOH is diluted in Dextrose Agar (previously melted and maintained at 50° C.) in successive stages so as to obtain the following concentrations: 64-32-16-8-4-2-1-0.5-0.25-0.125 μg of product per ml of medium.

Subsequently, each concentration of each product is dispensed into 10 cm diameter Petri dishes, in quantities of 10 ml of medium per dish, there being as many dishes as there are microorganisms for testing.

Once the medium has cooled, the dishes are seeded with the inocula in quantities of 0.4 ml of inoculum per dish. They are spread with a Driglasky loop and the supernatant is collected. The seeded dishes are incubated at 37° C. for 20 hours.

Results

The results obtained are described in the following tables. The activities of the compounds "in vitro" are compared with that of pipemidic acid.

| MICROORGANISMS | ipemidic acid | EXAMPLES 2 | 5 | 6 | 7 | 8 |
|---|---|---|---|---|---|---|
| Bacillus subtilis ATCC 6633 | 8 | ≦0.015 | 8 | 0.06 | 0.06 | ≦0.03 |
| Bacillus cereus ATCC 11778 | 16 | 0.3 | 64 | 0.25 | 0.50 | 0.25 |
| Strep. faecalis ATCC 10541 | >64 | 0.5 | 64 | 0.50 | 4 | 1 |
| Staph. aureus ATCC 25178 | 64 | 0.06 | 64 | 0.25 | 1 | 0.25 |
| Staph. epidermidis ATCC 155-1 | 64 | 0.12 | 64 | 0.50 | 0.50 | 0.25 |
| Ps. aeruginosa ATCC 9721 | 32 | 1.0 | 64 | 2 | 4 | 1 |
| Ps. aeruginosa ATCC 10145 | 32 | 2.0 | 64 | 4 | 8 | 4 |
| Citr. freundii ATCC 11606 | 4 | 0.06 | 64 | 0.5 | 1 | 0.5 |
| Morg. morganii ATCC 8019 | 8 | 0.6 | 64 | 0.25 | 1 | 0.5 |
| Proteus vulgaris ATCC 8427 | 16 | 0.6 | 64 | 0.25 | 1 | 0.5 |
| Kleb. pneumoniae ATCC 10031 | 2 | ≦0.015 | 64 | 0.06 | 0.50 | 0.5 |
| Sal. typhimurium ATCC 14028 | 8 | 0.12 | 64 | 0.5 | 1 | 0.5 |
| Sal. typhi ATCC 6539 | 4 | 0.06 | 64 | 0.25 | 1 | 0.5 |
| Escherichia coli ATCC 10799 | 16 | 0.12 | 64 | 0.50 | 1 | 0.5 |
| Escherichia coli ATCC 23559 | 2 | 0.06 | 64 | 0.25 | 1 | 0.5 |
| Ent. aerogenes ATCC 15038 | 32 | 0.12 | 64 | 0.50 | 1 | 0.5 |
| Ent. cloacae ATCC 23355 | 8 | 0.06 | 64 | 0.25 | 1 | 0.5 |
| Serr. marcescens ATCC 13880 | 16 | 0.25 | 64 | 1 | 1 | 0.5 |
| Shigella flexnerii ATCC 12022 | 4 | 0.06 | 64 | 0.25 | 0.50 | 0.25 |
| MICROORGANISMS | 9 | 10 | 11 | 12 | 13 | 14 |
| Bacillus subtilis ATCC 6633 | 0.06 | 0.06 | ≦0.03 | 0.12 | 0.5 | ≦0.03 |
| Bacillus cereus ATCC 11778 | 1 | 0.12 | 0.12 | 0.5 | 0.5 | 0.25 |
| Strep. faecalis ATCC 10541 | 1 | 0.12 | 0.5 | 2 | 2 | 1 |
| Staph. aureus ATCC 25178 | 0.25 | 0.12 | 0.06 | 0.05 | 1 | 0.25 |
| Staph. epidermidis ATCC 155-1 | 1 | 0.12 | 0.06 | 0.5 | 0.5 | 0.12 |
| Ps. aeruginosa ATCC 9721 | 1 | 1 | 4 | 2 | 2 | 1 |
| Ps. aeruginosa ATCC 10145 | 4 | 2 | 8 | 4 | 8 | 2 |
| Citr. freundii ATCC 11606 | 1 | 0.25 | 0.5 | 0.5 | 1 | 0.25 |
| Morg. morganii ATCC 8019 | 1 | 0.25 | 0.5 | 0.5 | 1 | 0.25 |
| Proteus vulgaris ATCC 8427 | 1 | 1 | 0.25 | 1 | 1 | 0.25 |
| Kleb. pneumoniae | 1 | 0.25 | ≦0.03 | 0.5 | 1 | 0.25 |

| | | | | | | |
|---|---|---|---|---|---|---|
| ATCC 10031 | | | | | | |
| *Sal. typhimurium* | 1 | 0.25 | 4 | 1 | 1 | 0.5 |
| ATCC 14028 | | | | | | |
| *Sal. typhi* | 1 | 0.25 | 0.5 | 0.5 | 1 | 0.25 |
| ATCC 6539 | | | | | | |
| *Escherichia coli* | 1 | 0.5 | 0.25 | 0.5 | 1 | 0.5 |
| ATCC 10799 | | | | | | |
| *Escherichia coli* | 0.5 | 0.25 | 0.25 | 0.5 | 1 | 0.25 |
| ATCC 23559 | | | | | | |
| *Ent. aerogenes* | 1 | 0.25 | 0.5 | 0.5 | 1 | 0.25 |
| ATCC 15038 | | | | | | |
| *Ent. cloacae* | 1 | 0.25 | 0.5 | 0.5 | 1 | 0.25 |
| ATCC 23355 | | | | | | |
| *Serr. marcescens* | 1 | 0.5 | 2 | 1 | 2 | 0.5 |
| ATCC 13880 | | | | | | |
| *Shigella flexnerii* | 1 | 0.25 | 0.25 | 0.12 | 1 | 0.25 |
| ATCC 12022 | | | | | | |

| | EXAMPLES | | | | | |
|---|---|---|---|---|---|---|
| MICROORGANISMS | 15 | 16 | 18 | 20 | 22 | 23 |
| *Bacillus subtilis* | 0.06 | ≦0.03 | ≦0.03 | 0.12 | 0.12 | ≦0.03 |
| ATCC 6633 | | | | | | |
| *Bacillus cereus* | 0.25 | 0.12 | 0.12 | 0.12 | 0.50 | 0.12 |
| ATCC 11778 | | | | | | |
| *Strep. faecalis* | 1 | 0.12 | 1.0 | 2.0 | 2.0 | 0.25 |
| ATCC 10541 | | | | | | |
| *Staph. aureus* | 0.25 | 0.12 | 0.12 | 0.12 | 0.5 | 0.12 |
| ATCC 25178 | | | | | | |
| *Staph. epidermidis* | 0.25 | 0.12 | 0.12 | 0.12 | 0.5 | 0.12 |
| ATCC 155-1 | | | | | | |
| *Ps. aeruginosa* | 2 | 0.5 | 1.0 | 2.0 | 2.0 | 0.50 |
| ATCC 9721 | | | | | | |
| *Ps. aeruginosa* | 2 | 0.5 | 2.0 | 2.0 | 2.0 | 0.50 |
| ATCC 10145 | | | | | | |
| *Citr. freundii* | 0.12 | 0.06 | 0.12 | 0.12 | 0.125 | ≦0.03 |
| ATCC 11606 | | | | | | |
| *Morg. morganii* | 0.12 | 0.06 | 0.25 | 0.25 | 0.125 | ≦0.03 |
| ATCC 8019 | | | | | | |
| *Proteus vulgaris* | 0.25 | 0.25 | 0.12 | 1.0 | 1.0 | 0.06 |
| ATCC 8427 | | | | | | |
| *Kleb. pneumoniae* | 0.25 | 0.06 | 0.12 | ≦0.03 | ≦0.03 | ≦0.03 |
| ATCC 10031 | | | | | | |
| *Sal. typhimurium* | 0.25 | 0.06 | 0.12 | 0.5 | 1.0 | 0.06 |
| ATCC 14028 | | | | | | |
| *Sal. typhi* | 0.25 | ≦0.03 | 0.12 | 0.5 | 0.5 | ≦0.03 |
| ATCC 6539 | | | | | | |
| *Escherichia coli* | 0.25 | 0.06 | 0.25 | 0.5 | 0.5 | 0.06 |
| ATCC 10799 | | | | | | |
| *Escherichia coli* | 0.12 | ≦0.03 | 0.12 | 0.25 | 0.12 | ≦0.03 |
| ATCC 23559 | | | | | | |
| *Ent. aerogenes* | 0.25 | 0.06 | 0.12 | 0.25 | 0.25 | ≦0.03 |
| ATCC 15038 | | | | | | |
| *Ent. cloacae* | 0.25 | ≦0.03 | 0.12 | 0.25 | 0.12 | ≦0.03 |
| ATCC 23355 | | | | | | |
| *Serr. marcescens* | 0.50 | 0.12 | 0.25 | 0.50 | 0.25 | 0.12 |
| ATCC 13880 | | | | | | |
| *Shigella flexnerii* | 0.12 | ≦0.03 | 0.06 | 0.12 | 0.12 | ≦0.03 |
| ATCC 12022 | | | | | | |

| | EXAMPLES | | | | | |
|---|---|---|---|---|---|---|
| MICROORGANISMS | 26 | 27 | 28 | 29 | 32 | 33 |
| *Bacillus subtilis* | 0.25 | 0.12 | ≦0.03 | 2 | 0.06 | 0.12 |
| ATCC 6633 | | | | | | |
| *Bacillus cereus* | 0.50 | 0.25 | 0.06 | 4 | 0.12 | 0.12 |
| ATCC 11778 | | | | | | |
| *Strep. faecalis* | 2.0 | 1.0 | 2 | 4 | 0.5 | 1.0 |
| ATCC 10541 | | | | | | |
| *Staph. aureus* | 1.0 | 0.25 | 0.03 | 4 | 0.25 | 0.25 |
| ATCC 25178 | | | | | | |
| *Staph. epidermidis* | 0.5 | 0.25 | 0.03 | 4 | 0.25 | 0.5 |
| ATCC 155-1 | | | | | | |
| *Ps. aeruginosa* | 4.0 | 1.0 | 2 | ≧16 | 0.5 | 4.0 |
| ATCC 9721 | | | | | | |
| *Ps. aeruginosa* | 4.0 | 2.0 | 2 | ≧16 | 1.0 | 4.0 |
| ATCC 10145 | | | | | | |
| *Citr. freundii* | 1.0 | 0.25 | 1 | 16 | 0.12 | 0.25 |
| ATCC 11606 | | | | | | |
| *Morg. morganii* | 1.0 | 0.25 | 0.5 | 8 | 0.12 | 0.5 |
| ATCC 8019 | | | | | | |
| *Proteus vulgaris* | 1.0 | 0.25 | 0.12 | 8 | 0.12 | 0.25 |
| ATCC 8427 | | | | | | |
| *Kleb. pneumoniae* | 0.25 | 0.25 | ≦0.03 | 8 | 0.25 | 0.5 |

| | -continued | | | | | |
|---|---|---|---|---|---|---|
| ATCC 10031 | | | | | | |
| Sal. typhimurium ATCC 14028 | 1.0 | 0.5 | 1 | 16 | 0.25 | 0.5 |
| Sal. typhi ATCC 6539 | 1.0 | 0.5 | 1 | 16 | 0.25 | 0.5 |
| Escherichia coli ATCC 10799 | 1.0 | 0.5 | 1 | 16 | 0.25 | 0.5 |
| Escherichia coli ATCC 23559 | 0.5 | 0.25 | 0.5 | 8 | 0.12 | 0.12 |
| Ent. aerogenes ATCC 15038 | 1.0 | 0.25 | 1 | 16 | 0.25 | 0.5 |
| Ent. cloacae ATCC 23355 | 0.5 | 0.25 | 1 | 4 | 0.25 | 0.25 |
| Serr. marcescens ATCC 13880 | 2.0 | 0.5 | 1 | 16 | 0.5 | 1.0 |
| Shigella flexnerii ATCC 12022 | 0.5 | 0.25 | 0.5 | 4 | 0.06 | 0.25 |

| | EXAMPLES | | | | | |
|---|---|---|---|---|---|---|
| MICROORGANISMS | 35 | 36 | 37 | 38 | 39 | 40 |
| Bacillus subtilis ATCC 6633 | 0.25 | 0.25 | 0.25 | 0.12 | 0.06 | 0.06 |
| Bacillus cereus ATCC 11778 | 0.5 | 1 | 1 | 0.25 | 0.25 | 0.12 |
| Strep. faecalis ATCC 10541 | 0.25 | 0.25 | 2 | 0.12 | 1 | 0.5 |
| Staph. aureus ATCC 25178 | 0.25 | 0.5 | 1 | 0.25 | 0.25 | 0.12 |
| Staph. epidermidis ATCC 155-1 | 0.5 | 0.5 | 1 | 0.25 | 0.25 | 0.12 |
| Ps. aeruginosa ATCC 9721 | 4.0 | 2 | 4 | 2 | 2 | 1.0 |
| Ps. aeruginosa ATCC 10145 | 2.0 | 2 | 4 | 2 | 2 | 0.5 |
| Citr. freundii ATCC 11606 | 0.25 | 0.25 | 0.5 | 0.12 | 0.12 | 0.06 |
| Morg. morganii ATCC 8019 | 0.5 | 0.25 | 0.5 | 0.25 | 0.25 | 0.06 |
| Proteus vulgaris ATCC 8427 | 0.5 | 1 | 1 | 0.25 | 0.5 | 0.06 |
| Kleb. pneumoniae ATCC 10031 | 0.5 | 0.5 | 0.5 | 0.12 | 0.25 | 0.12 |
| Sal. typhimurium ATCC 14028 | 0.5 | 1 | 0.5 | 0.25 | 0.25 | 0.12 |
| Sal. typhi ATCC 6539 | 0.25 | 0.5 | 0.5 | 0.25 | 0.12 | 0.12 |
| Escherichia coli ATCC 10799 | 0.5 | 1 | 1 | 0.25 | 0.25 | 0.12 |
| Escherichia coli ATCC 23559 | 0.25 | 0.5 | 0.5 | 0.12 | 0.12 | 0.06 |
| Ent. aerogenes ATCC 15038 | 0.5 | 0.5 | 1 | 0.25 | 0.25 | 0.12 |
| Ent. cloacae ATCC 23355 | 0.25 | 0.5 | 1 | 0.25 | 0.12 | 0.12 |
| Serr. marcescens ATCC 13880 | 1 | 1 | 1 | 1 | 1 | 0.25 |
| Shigella flexnerii ATCC 12022 | 0.25 | 0.25 | 0.5 | 0.12 | 0.06 | 0.06 |

| | EXAMPLES | | | | | |
|---|---|---|---|---|---|---|
| MICROORGANISMS | 41 | 42 | 43 | 44 | 45 | 46 |
| Bacillus subtilis ATCC 6633 | 0.25 | 0.06 | ≦0.03 | ≦0.03 | ≦0.03 | ≦0.03 |
| Bacillus cereus ATCC 11778 | 1 | 0.2 | 0.25 | 0.12 | 0.12 | 0.12 |
| Strep faecalis ATCC 10541 | 4 | 2 | 1 | 1 | 0.12 | 0.12 |
| Staph. aureus ATCC 25178 | 1 | 0.12 | 0.25 | 0.12 | 0.12 | 0.12 |
| Staph. epidermidis ATCC 155-1 | 1 | 0.12 | 0.25 | 0.12 | 0.12 | 0.12 |
| Ps. aeruginosa ATCC 9721 | 2 | 2 | 1 | 2 | 0.5 | 0.5 |
| Ps. aeruginosa ATCC 10145 | 4 | 2 | 2 | 2 | 0.5 | 0.5 |
| Citr. freundii ATCC 11606 | 1 | 0.12 | 0.06 | 0.12 | 0.06 | 0.06 |
| Morg. morganii ATCC 8019 | 1 | 0.25 | 0.12 | 0.12 | 0.06 | 0.06 |
| Proteus vulgaris ATCC 8427 | 1 | 0.25 | 0.25 | 0.12 | 0.25 | 0.25 |
| Kleb. pneumoniae | 1 | 0.12 | 0.06 | ≦0.03 | 0.06 | 0.06 |

-continued

| | | | | | | |
|---|---|---|---|---|---|---|
| ATCC 10031 | | | | | | |
| Sal. typhimurium | 1 | 0.12 | 0.12 | 0.12 | 0.06 | 0.06 |
| ATCC 14028 | | | | | | |
| Sal. typhi | 1 | 0.12 | 0.06 | 0.06 | ≦0.03 | ≦0.03 |
| ATCC 6539 | | | | | | |
| Escherichia coli | 1 | 0.25 | 0.12 | 0.12 | 0.06 | 0.06 |
| ATCC 10799 | | | | | | |
| Escherichia coli | 1 | 0.12 | 0.06 | 0.06 | ≦0.03 | ≦0.03 |
| ATCC 23559 | | | | | | |
| Ent. aerogenes | 1 | 0.12 | 0.2 | 0.12 | 0.06 | 0.06 |
| ATCC 15038 | | | | | | |
| Ent. cloacae | 1 | 0.12 | 0.06 | 0.06 | 0.03 | 0.03 |
| ATCC 23355 | | | | | | |
| Serr. marcescens | 1 | 0.5 | 0.25 | 0.25 | 0.12 | 0.12 |
| ATCC 13880 | | | | | | |
| Shigella flexnerii | 1 | 0.06 | 0.06 | 0.06 | ≦0.03 | ≦0.03 |
| ATCC 12022 | | | | | | |

| | EXAMPLES | | |
|---|---|---|---|
| MICROORGANISMS | 47 | 48 | 49 |
| Bacillus subtilis | 0.06 | ≦0.05 | ≦0.03 |
| ATCC 6633 | | | |
| Bacillus cereus | 0.25 | 0.12 | 0.12 |
| ATCC 11778 | | | |
| Strep. faecalis | 1.0 | 1.0 | 0.5 |
| ATCC 10541 | | | |
| Staph. aureus | 0.25 | 0.25 | 0.25 |
| ATCC 25178 | | | |
| Staph. epidermidis | 0.12 | 0.12 | 0.12 |
| ATCC 155-1 | | | |
| Ps. aeruginosa | 1.0 | 0.5 | 0.5 |
| ATCC 9721 | | | |
| Ps. aeruginosa | 0.5 | 0.5 | 0.25 |
| ATCC 10145 | | | |
| Citr. freundii | ≦0.03 | ≦0.03 | ≦0.03 |
| ATCC 11606 | | | |
| Morg. morganii | 0.06 | ≦0.03 | ≦0.03 |
| ATCC 8019 | | | |
| Proteus vulgaris | 0.5 | 0.25 | 0.12 |
| ATCC 8427 | | | |
| Kleb. pneumoniae | ≦0.03 | ≦0.03 | ≦0.03 |
| ATCC 10031 | | | |
| Sal. typhimurium | 0.06 | 0.06 | ≦0.03 |
| ATCC 14028 | | | |
| Sal. typhi | ≦0.03 | ≦0.03 | ≦0.03 |
| ATCC 6539 | | | |
| Escherichia coli | 0.06 | 0.06 | 0.06 |
| ATCC 10799 | | | |
| Escherichia coli | ≦0.03 | ≦0.03 | ≦0.03 |
| ATCC 23559 | | | |
| Ent. aerogenes | 0.06 | ≦0.03 | ≦0.03 |
| ATCC 15038 | | | |
| Ent. cloacae | ≦0.03 | ≦0.03 | ≦0.03 |
| ATCC 23355 | | | |
| Serr. marcescens | 0.12 | 0.12 | 0.12 |
| ATCC 13880 | | | |
| Shigella flexnerii | <0.03 | ≦0.03 | ≦0.03 |
| ATCC 12022 | | | |

Taking account of their good pharmacological properties, derivatives of general formula I are therefore likely to be used in human medicine and/or veterinary medicine to treat systemic or localised acute, chronic and recurring infections, caused by Gram-positive and Gram-negative microorganisms that are sensitive to the products which are the subject of the present invention, in the gastrointestinal or genito-urinary tracts, the respiratory system, the skin and soft tissues, and also neurological and odonto-stomatological infections.

In human therapy, the proposed dose of the derivatives of the present invention is approximately between 400 and 1200 mg/day for an adult, administered for example as tablets or capsules. This dosage may however be varied in relation to the gravity of the illness.

Two particular pharmaceutical forms of the derivatives which are the subject of the present invention will be shown hereinafter, by way of example.

| Example of a formula per tablet | |
|---|---|
| Compound of example 2 | 0.400 g |
| Carboxymethylstarch | 0.018 g |
| Polyvinylpyrrolidone K29-32 | 0.030 g |
| Microcrystalline cellulose | 0.146 g |
| Colloidal silica | 0.003 g |
| Magnesium stearate | 0.003 g |
| | 0.600 g |

| Example of a formula per gelatin capsule | |
|---|---|
| Compound of example 16 | 0.400 g |
| Microcrystalline cellulose | 0.0356 g |
| Colloidal silica | 0.0022 g |
| Magnesium stearate | 0.0022 g |

| Example of a formula per gelatin capsule | |
|---|---|
| | 0.440 g |

We claim:

1. New heterocyclic compounds characterised in that they correspond to formula I

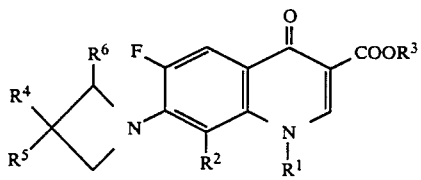

where

R¹ represents a lower alkenyl or alkyl radical, a haloalkyl radical, a cycloalkyl radical, an aminoalkyl radical, an aryl radical or a substituted aryl radical, particularly one having one or more fluorine atom substituents, R² represents a hydrogen atom, a halogen atom, or R¹ and R² may together form an X group;

R³ represents a hydrogen atom or a lower alkyl radical;

R⁴ and R⁵ and R⁶ independently represent a hydrogen atom, a lower alkyl radical, a hydroxyl radical, an amino radical, an aminoalkyl radical, an alkylamino radical, a dialkylamino radical, an alkylaminoalkyl radical, an alkoxy radical, a mesyloxy radical, a hydroxyalkyl radical, a cyano radical, an acylaminoalkyl radical, a carboxylic radical, a carboxamido radical, a carboxyalkyl radical, a halogen atom, an alkylcarboxy radical for example acetoxy, an acetamido radical or an acetamidoalkyl radical, in these last two radicals the terminal free alkyl group may be fluorinated and the nitrogen atom in the acetamidoalkyl radical may carry an alkyl substituent;

X represents —CH₂—CH₂—CHR⁷—, —O—CH₂—CHR⁷— or

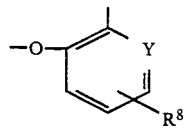

where

R⁷ represents a hydrogen atom or a lower alkyl radical,

R⁸ represents a hydrogen atom or a halogen atom, and Y represents CH or N, with the exception however of compounds of formula (I) in which:

R¹ and R² together form a link represented by the group —O—CH₂—CH(CH₃)— and

R³, R⁴ and R⁶ represent a hydrogen atom, and R⁵ represents a hydroxyl radical (OH) or a hydroxymethyl radical (CH₂OH), and of the compound of formula (I) in which:

R¹ represents an ethyl radical

R² represents a fluorine atom

R³, R⁴ and R⁶ represent hydrogen atoms, and

R⁵ represents an ethylaminomethyl radical (CH₃CH₂NHCH₂).

2. Heterocyclic compounds according to claim 1, characterised in that they correspond to general formula (I) with R⁶ and R³ represented by a hydrogen atom and R¹, R², R⁴ and R⁵ having the same meaning as hereinbefore.

3. Heterocyclic compounds according to claims 1 or 2, characterised in that they correspond to general formula (Ia)

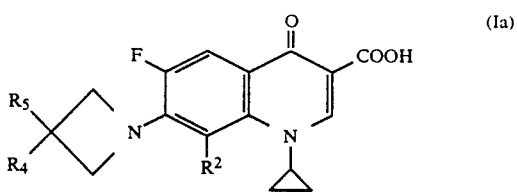

in which R², R⁴ and R⁵ have the same meaning as hereinfore.

4. Compounds corresponding to general formula (I) selected from the following group:

1-(4-fluorophenyl)-6,8-difluoro-7-(3-methyl-3-trifluoroacetamido-1-azetidinyl)-1,4-dihydro-4-oxo-3-quinolinecarboxylic acid, 1-(4-fluorophenyl)-6,8-difluoro-7-(3-amino-3-methyl-1-azetidinyl)-1,4-dihydro-4-oxo-3-quinolinecarboxylic acid.

1-ethyl-6,8-difluoro-1,4-dihydro-4-oxo-7-(3-methyl-3-trifluoroacetamido-1-azetidinyl)-3-quinolinecarboxylic acid, 1-ethyl-6,8-difluoro-7-(3-amino-3-methyl-1-azetidinyl)-1,4-dihydro-4-oxo-3-quinolinecarboxylic acid,

[S]-(—)-9-fluoro-3-methyl-7-oxo-2,3-dihydro-7H-pyrido[1,2,3-de][1,4]benzoxazine-10-(3-amino-3-methyl-1-azetidinyl)-6-carboxylic acid,

[R]-(+)-9-fluoro-3-methyl-7-oxo-2,3-dihydro-7H-pyrido[1,2,3-de][1,4]benzoxazine-10-(3-amino-3-methyl-1-azetidinyl)-6-carboxylic acid, 1-ethyl-6-fluoro-7-(3-amino-3-methyl-1-azetidinyl)-1,4-dihydro-4-oxo-3-quinolinecarboxylic acid, 1-(2-fluoroethyl)-6-fluoro-7-(3-methyl-3-amino-1-azetidinyl)-1,4-dihydro-4-oxo-3-quinolinecarboxylic acid, 1-(2,4-difluorophenyl)-6-fluoro-7-(3-methyl-3-amino-1-azetidinyl)-1,4-dihydro-4-oxo-3-quinolinecarboxylic acid, 1-(2-fluoroethyl)-6,8-difluoro-7-(3-amino-3-methyl-1-azetidinyl)-1,4-dihydro-4-oxo-3-quinolinecarboxylic acid, 1-(4-fluorophenyl)-6-fluoro-7-(3-amino-3-methyl-1-azetidinyl)-1,4-dihydro-4-oxo-3-quinolinecarboxylic acid, 1-(2,4-difluorophenyl)-6,8-difluoro-7-(3-methyl-3-trifluoroacetamido-1-azetidinyl)-1,4-dihydro-4-oxo-3-quinolinecarboxylic acid, 1-(2,4-difluorophenyl)-6,8-difluoro-7-(3-amino-3-methyl-1-azetidinyl)-1,4-dihydro-4-oxo-3-quinolinecarboxylic acid.

5. Compounds corresponding to general formula I, selected from the following group:

ethyl 1-cyclopropyl-6,8-difluoro-7-(3-hydroxy-1-azetidinyl)-1,4-dihydro-4-oxo-3-quinolinecarboxylate, 1-cyclopropyl-6,8-difluoro-7-(3-hydroxy-1-azetidinyl)-1,4-dihydro-4-oxo-3-quinolinecarboxylic acid, ethyl 1-cyclopropyl-6,8-difluoro-7-(3-mesyloxy-1-azetidinyl)-1,4-dihydro-4-oxo-3-quinolinecarboxylate, ethyl 7-(3-acetylaminomethyl-1-azetidinyl)-1-cyclopropyl-6,8-difluoro-1,4-dihydro-4-oxo-3-quinolinecarboxylate, 1-cyclopropyl-6,8-difluoro-7-(3-carboxy-1-azetidinyl)-1,4-dihydro-4-oxo-3-quinolinecarboxylic acid, 1-cyclopropyl-6,8-difluoro-7-(3-carbamoyl-1-azetidinyl)-1,4-dihydro-4-oxo-3-quinolinecarboxylic acid, 1-cyclopropyl-6,8-difluoro-7-(3-cyano-1-azetidinyl)-1,4-dihydro-4-oxo-3-quinolinecarboxylic acid, 1-cyclopropyl-6,8-difluoro-7-(3-methyl-3-hydroxy-1-azetidinyl)-1,4-dihydro-4-oxo-3-quinolinecarboxylic acid, 7-(3-trifluoroacetamidomethyl-1-azetidinyl)-1-cyclopropyl-6,8-difluoro-1,4-dihydro-4-oxo-3-quinolinecarboxylic acid, 7-(3-aminomethyl-1-azetidinyl)-1-cyclopropyl-6,8-difluoro-1,4-dihydro-4-oxo-3-quinolinecarboxylic acid, 1-cyclopropyl-6,8-difluoro-7-(3-mesyloxy-1-azetidinyl)-1,4-dihydro-4-oxo-3-quinolinecarboxylic acid, 7-[3-(N'-ethyl-N'-trifluoroacetamidomethyl)-1-azetidinyl]-6,8-difluoro-1,4-dihydro-1-cyclopropyl-4-oxo-3-quinolinecarboxylic acid, 7-(3-N'-ethylaminomethyl-1-azetidinyl)-6,8-difluoro-1,4-dihydro-1-cyclopropyl-4-oxo-3-quinolinecarboxylic acid, 1-cyclopropyl-6,8-difluoro-1,4-dihydro-7-(1-azetidinyl)-4-oxo-3-quinolinecarboxylic acid, 1-cyclopropyl-6,8-difluoro-7-(3-methyl-3-trifluoroacetamido-1-azetidinyl)-4-oxo-3-quinolinecarboxylic acid, 1-cyclopropyl-6,8-difluoro-1,4-dihydro-7-(3-methyl-3-amino-1-azetidinyl)-4-oxo-3-quinolinecarboxylic acid, 1-cyclopropyl-6,8-difluoro-7-(3-acetoxy-1-azetidinyl)-1,4-dihydro-4-oxo-3-quinolinecarboxylic acid, 1-cyclopropyl-6-fluoro-7-(3-hydroxy-1-azetidinyl)-1,4-dihydro-4-oxo-3-quinolinecarboxylic acid, 1-cyclopropyl-6,8-difluoro-7-(3-amino-1-azetidinyl)-1,4-dihydro-4-oxo-3-quinolinecarboxylic acid, 1-cyclopropyl-6,8-difluoro-7-(3-trifluoroacetamidomethyl-3-methyl-1-azetidinyl)-1,4-dihydro-4-oxo-3-quinolinecarboxylic acid, 1-cyclopropyl-6,8-difluoro-7-(3-N-ethyl-trifluoroacetamidomethyl-3-methyl-1-azetidinyl)-1,4-dihydro-4-oxo-3-quinolinecarboxylic acid, 1-cyclopropyl-6,8-difluoro-1,4-dihydro-4-oxo-7-(3-aminomethyl-3-methyl-1-azetidinyl)-3-quinolinecarboxylic acid, 1-cyclopropyl-6,8-difluoro-7-(3-ethylaminomethyl-3-methyl-1-azetidinyl)-1,4-dihydro-4-oxo-3-quinolinecarboxylic acid, 1-cyclopropyl-6-fluoro-7-(3-trifluoroacetamidomethyl-3-methyl-1-azetidinyl)-1,4-dihydro-4-oxo-3-quinolinecarboxylic acid, 1-cyclopropyl-6-fluoro-7-(3-trifluoroacetamidoethylaminomethyl-3-methyl-1-azetidinyl)-1,4-dihydro-4-oxo-3-quinolinecarboxylic acid, 1-cyclopropyl-6-fluoro-1,4-dihydro-4-oxo-7-(3-aminomethyl-3-methyl-1-azetidinyl)-3-quinolinecarboxylic acid, 1-cyclopropyl-6-fluoro-7-(3-ethylaminomethyl-3-methyl-1-azetidinyl)-1,4-dihydro-4-oxo-3-quinolinecarboxylic acid, 1-cyclopropyl-6,8-difluoro-1,4-dihydro-4-oxo-7-(3-methyl-3-N,N-dimethylamino-1-azetidinyl)-3-quinolinecarboxylic acid, 1-cyclopropyl-6-fluoro-7-(3-amino-3-methyl-1-azetidinyl)-1,4-dihydro-4-oxo-3-quinolinecarboxylic acid, 1-cyclopropyl-6,8-difluoro-7-(3-dimethylamino-1-azetidinyl)-1,4-dihydro-4-oxo-3-quinolinecarboxylic acid, 1-cyclopropyl-6-fluoro-7-(3-dimethylamino-1-azetidinyl)-1,4-dihydro-4-oxo-3-quinolinecarboxylic acid 1-cyclopropyl-6,8-difluoro-7-(3-amino-3-methyl-1-azetidinyl)-1,4-dihydro-4-oxo-3-quinolinecarboxylic acid hydrochloride Sodium salt of 1-cyclopropyl-6,8-difluoro-7-(3-amino-3-methyl-1-azetidinyl)-1,4-dihydro-4-oxo-3-quinolinecarboxylic acid.

1-cyclopropyl-6,8-difluoro-7-(3-methylamino-1-azetidinyl 1,4-dihydro-4-oxo-3-quinolinecarboxylic acid, 1-cyclopropyl-6-fluoro-7-(3-methylamino-1-azetidinyl)-1,4-dihydro-4-oxo-3-quinolinecarboxylic acid, 1-cyclopropyl-6-fluoro-7-(3-amino-1-azetidinyl)-1,4-dihydro-4-oxo-3-quinolinecarboxylic acid.

6. Process for preparating derivatives of formula I according to claims 1 or 2, characterised in that it comprises reacting a heterocyclic compound of formula II, where $R^1$, $R^2$ and $R^3$ have the same meaning as hereinbefore, and Z represents an amino radical, with a compound represented by formula (IV)

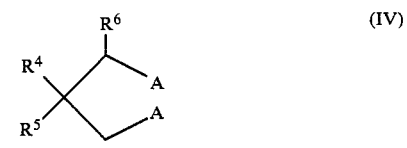

where $R^4$ and $R^5$ and $R^6$ have the same meaning as hereinbefore, and A represents a halogen atom, a hydroxyl radical, a lower alkylsulphonyloxy radical or an aryl sulphonyloxy radical.

7. Pharmaceutical compositions, characterised by the fact that they contain, besides an acceptable pharmaceutical support, at least one compound of general formula (I) or a physiologically acceptable salt of such a compound, according to claims 1 or 2.

8. The use of a compound according to claims 1 or 2 as an antibacterial agent.

* * * * *